(12) United States Patent
Grauzer et al.

(10) Patent No.: US 9,922,502 B2
(45) Date of Patent: *Mar. 20, 2018

(54) APPARATUS, SYSTEM, METHOD, AND COMPUTER-READABLE MEDIUM FOR CASINO CARD HANDLING WITH MULTIPLE HAND RECALL FEATURE

(71) Applicant: Bally Gaming, Inc., Las Vegas, NV (US)

(72) Inventors: Attila Grauzer, Las Vegas, NV (US); Feraidoon Bourbour, Edina, MN (US); Mark L. Yoseloff, Henderson, NV (US)

(73) Assignee: Balley Gaming, Inc., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/483,840

(22) Filed: Apr. 10, 2017

(65) Prior Publication Data

US 2017/0213423 A1 Jul. 27, 2017

Related U.S. Application Data

(63) Continuation of application No. 15/043,241, filed on Feb. 12, 2016, now Pat. No. 9,633,523, which is a
(Continued)

(51) Int. Cl.
*G07F 17/32* (2006.01)
*A63F 1/12* (2006.01)
*A63F 1/14* (2006.01)

(52) U.S. Cl.
CPC ............ *G07F 17/3293* (2013.01); *A63F 1/12* (2013.01); *A63F 1/14* (2013.01); *G07F 17/3216* (2013.01); *G07F 17/3225* (2013.01)

(58) Field of Classification Search
USPC ............................ 463/11, 12, 46; 273/149 R
See application file for complete search history.

(56) References Cited

U.S. PATENT DOCUMENTS 130,281 A 8/1872 Coughlin
205,030 A 6/1878 Ash
(Continued)

FOREIGN PATENT DOCUMENTS

AU 2383667 A 1/1969
AU 5025479 A1 3/1980
(Continued)

OTHER PUBLICATIONS

European Search Report for European Application No. 12 152 303, dated Apr. 16, 2012, 3 pages.
(Continued)

*Primary Examiner* — Pierre E Elisca
(74) *Attorney, Agent, or Firm* — TraskBritt

(57) ABSTRACT

Apparatuses, systems, methods, and computer-readable media are disclosed for detecting, storing, and retrieving information about the composition of present and past hands of cards in a casino table game. The method includes causing a card-handling device to substantially automatically generate a plurality of hands wherein each hand includes one or more cards. Card information is identified that includes a rank and a suit of each card as each card moves through the card-handling device. A play history is maintained of a card composition of more than one round wherein the card composition of each round includes the cards in each hand of each round. The card information of at least one hand from at least one round may be displayed.

20 Claims, 10 Drawing Sheets

Related U.S. Application Data continuation of application No. 14/330,964, filed on Jul. 14, 2014, now Pat. No. 9,259,640, which is a continuation of application No. 13/311,166, filed on Dec. 5, 2011, now Pat. No. 8,777,710, which is a continuation of application No. 11/810,864, filed on Jun. 6, 2007, now Pat. No. 8,070,574.

(56) References Cited

U.S. PATENT DOCUMENTS

| | | |
|---|---|---|
| 609,730 A | 8/1898 | Booth |
| 673,154 A | 4/1901 | Bellows |
| 793,489 A | 6/1905 | Williams |
| 892,389 A | 7/1908 | Bellows |
| 1,014,219 A | 1/1912 | Hall |
| 1,043,109 A | 11/1912 | Hurm |
| 1,157,898 A | 10/1915 | Perret |
| 1,992,085 A | 2/1925 | McKay |
| 1,556,856 A | 10/1925 | Lipps |
| 1,850,114 A | 6/1929 | McCaddin |
| 1,757,553 A | 5/1930 | Gustav |
| 1,885,276 A | 11/1932 | McKay |
| 1,889,729 A | 11/1932 | Hammond |
| 1,955,926 A | 4/1934 | Matthaey |
| 1,998,690 A | 4/1935 | Shepherd et al. |
| 2,001,220 A | 5/1935 | Smith |
| 2,001,918 A | 5/1935 | Nevius |
| 2,016,030 A | 10/1935 | Woodruff et al. |
| 2,043,343 A | 6/1936 | Warner |
| 2,060,096 A | 11/1936 | McCoy |
| 2,065,824 A | 12/1936 | Plass |
| 2,159,958 A | 5/1939 | Sachs |
| 2,185,474 A | 1/1940 | Nott |
| 2,254,484 A | 9/1941 | Hutchins |
| D132,360 S | 5/1942 | Gardner |
| 2,328,153 A | 8/1943 | Laing |
| 2,328,879 A | 9/1943 | Isaacson |
| D139,530 S | 11/1944 | Schindler |
| 2,364,413 A | 12/1944 | Wittel |
| 2,525,305 A | 10/1950 | Lombard |
| 2,543,522 A | 2/1951 | Cohen |
| 2,588,582 A | 3/1952 | Sivertson |
| 2,615,719 A | 10/1952 | Fonken |
| 2,659,607 A | 11/1953 | Skillman et al. |
| 2,661,215 A | 12/1953 | Stevens |
| 2,676,020 A | 4/1954 | Ogden |
| 2,692,777 A | 10/1954 | Miller |
| 2,701,720 A | 2/1955 | Ogden |
| 2,705,638 A | 4/1955 | Newcomb |
| 2,711,319 A | 6/1955 | Morgan et al. |
| 2,714,510 A | 8/1955 | Oppenlander et al. |
| 2,717,782 A | 9/1955 | Droll |
| 2,727,747 A | 12/1955 | Semisch, Jr. |
| 2,731,271 A | 1/1956 | Brown |
| 2,747,877 A | 5/1956 | Howard |
| 2,755,090 A | 7/1956 | Aldrich |
| 2,757,005 A | 7/1956 | Nothaft |
| 2,760,779 A | 8/1956 | Ogden et al. |
| 2,770,459 A | 11/1956 | Wilson et al. |
| 2,778,643 A | 1/1957 | Williams |
| 2,778,644 A | 1/1957 | Stephenson |
| 2,782,040 A | 2/1957 | Matter |
| 2,790,641 A | 4/1957 | Adams |
| 2,793,863 A | 5/1957 | Liebelt |
| 2,815,214 A | 12/1957 | Hall |
| 2,821,399 A | 1/1958 | Heinoo |
| 2,914,215 A | 11/1959 | Neidig |
| 2,937,739 A | 5/1960 | Levy |
| 2,950,005 A | 8/1960 | MacDonald |
| RE24,986 E | 5/1961 | Stephenson |
| 3,067,885 A | 12/1962 | Kohler |
| 3,107,096 A | 10/1963 | Osborn |
| 3,124,674 A | 3/1964 | Edwards et al. |
| 3,131,935 A | 5/1964 | Gronneberg |
| 3,147,978 A | 9/1964 | Sjostrand |
| D200,652 S | 3/1965 | Fisk |
| 3,222,071 A | 12/1965 | Lang |
| 3,235,741 A | 2/1966 | Plaisance |
| 3,288,308 A | 11/1966 | Gingher |
| 3,305,237 A | 2/1967 | Granius |
| 3,312,473 A | 4/1967 | Friedman et al. |
| 3,452,509 A | 7/1969 | Hauer |
| 3,530,968 A | 9/1970 | Palmer |
| 3,588,116 A | 6/1971 | Miura |
| 3,589,730 A | 6/1971 | Slay |
| 3,595,388 A | 7/1971 | Castaldi |
| 3,597,076 A | 8/1971 | Hubbard et al. |
| 3,618,933 A | 11/1971 | Roggenstein et al. |
| 3,627,331 A | 12/1971 | Erickson |
| 3,666,270 A | 5/1972 | Mazur |
| 3,680,853 A | 8/1972 | Houghton et al. |
| 3,690,670 A | 9/1972 | Cassady et al. |
| 3,704,938 A | 12/1972 | Fanselow |
| 3,716,238 A | 2/1973 | Porter |
| 3,751,041 A | 8/1973 | Seifert |
| 3,761,079 A | 9/1973 | Azure, Jr. |
| 3,810,627 A | 5/1974 | Levy |
| D232,953 S | 9/1974 | Oguchi |
| 3,861,261 A | 1/1975 | Maxey |
| 3,897,954 A | 8/1975 | Erickson et al. |
| 3,899,178 A | 8/1975 | Watanabe |
| 3,909,002 A | 9/1975 | Levy |
| 3,929,339 A | 12/1975 | Mattioli |
| 3,944,077 A | 3/1976 | Green |
| 3,944,230 A | 3/1976 | Fineman |
| 3,949,219 A | 4/1976 | Crouse |
| 3,968,364 A | 7/1976 | Miller |
| 4,023,705 A | 5/1977 | Reiner et al. |
| 4,033,590 A | 7/1977 | Pic |
| 4,072,930 A | 2/1978 | Lucero et al. |
| 4,088,265 A | 5/1978 | Garczynski |
| 4,151,410 A | 4/1979 | McMillan et al. |
| 4,159,581 A | 7/1979 | Lichtenberg |
| 4,162,649 A | 7/1979 | Thornton |
| 4,166,615 A | 9/1979 | Noguchi et al. |
| 4,232,861 A | 11/1980 | Maul |
| 4,280,690 A | 7/1981 | Hill |
| 4,283,709 A | 8/1981 | Lucero et al. |
| 4,310,160 A | 1/1982 | Willette et al. |
| 4,339,134 A | 7/1982 | Macheel |
| 4,339,798 A | 7/1982 | Hedges et al. |
| 4,361,393 A | 11/1982 | Noto |
| 4,368,972 A | 1/1983 | Naramore |
| 4,369,972 A | 1/1983 | Parker |
| 4,374,309 A | 2/1983 | Walton |
| 4,377,285 A | 3/1983 | Kadlic |
| 4,385,827 A | 5/1983 | Naramore |
| 4,388,994 A | 6/1983 | Suda et al. |
| 4,397,469 A | 8/1983 | Carter, III |
| 4,421,312 A | 12/1983 | Delgado et al. |
| 4,421,501 A | 12/1983 | Scheffer |
| D273,962 S | 5/1984 | Fromm |
| D274,069 S | 5/1984 | Fromm |
| 4,467,424 A | 8/1984 | Hedges et al. |
| 4,494,197 A | 1/1985 | Troy et al. |
| 4,497,488 A | 2/1985 | Plevyak et al. |
| 4,512,580 A | 4/1985 | Matviak |
| 4,513,969 A | 4/1985 | Samsel, Jr. |
| 4,515,367 A | 5/1985 | Howard |
| 4,531,187 A | 7/1985 | Uhland |
| 4,549,738 A | 10/1985 | Greitzer |
| 4,566,782 A | 1/1986 | Britt et al. |
| 4,575,367 A | 3/1986 | Karmel |
| 4,534,562 A | 5/1986 | Cuff et al. |
| 4,586,712 A | 5/1986 | Lorber et al. |
| 4,659,082 A | 4/1987 | Greenberg |
| 4,662,637 A | 5/1987 | Pfeiffer |
| 4,662,816 A | 5/1987 | Fabrig |
| 4,667,959 A | 5/1987 | Pfeiffer et al. |
| 4,741,524 A | 5/1988 | Bromage |
| 4,750,743 A | 6/1988 | Nicoletti |
| 4,755,941 A | 7/1988 | Bacchi |
| 4,759,448 A | 7/1988 | Kawabata |
| 4,770,412 A | 9/1988 | Wolfe |

(56) References Cited

U.S. PATENT DOCUMENTS

| | | |
|---|---|---|
| 4,770,421 A | 9/1988 | Hoffman |
| 4,807,884 A | 2/1989 | Breeding |
| 4,822,050 A | 4/1989 | Normand et al. |
| 4,832,342 A | 5/1989 | Plevyak et al. |
| 4,858,000 A | 8/1989 | Lu |
| 4,861,041 A | 8/1989 | Jones et al. |
| 4,876,000 A | 10/1989 | Mikhail |
| 4,900,009 A | 2/1990 | Kitahara et al. |
| 4,904,830 A | 2/1990 | Rizzuto |
| 4,921,109 A | 5/1990 | Hasuo et al. |
| 4,926,327 A | 5/1990 | Sidley |
| 4,948,134 A | 8/1990 | Suttle et al. |
| 4,951,950 A | 8/1990 | Normand et al. |
| 4,969,648 A | 11/1990 | Hollinger et al. |
| 4,993,587 A | 2/1991 | Abe |
| 4,995,615 A | 2/1991 | Cheng |
| 5,000,453 A | 3/1991 | Stevens et al. |
| 5,039,102 A | 8/1991 | Miller |
| 5,067,713 A | 11/1991 | Soules et al. |
| 5,078,405 A | 1/1992 | Jones et al. |
| 5,081,487 A | 1/1992 | Hoyer et al. |
| 5,102,293 A | 4/1992 | Schneider |
| 5,118,114 A | 6/1992 | Tucci |
| 5,121,192 A | 6/1992 | Kazui |
| 5,121,921 A | 6/1992 | Friedman et al. |
| 5,146,346 A | 9/1992 | Knoll |
| 5,154,429 A | 10/1992 | LeVasseur |
| 5,179,517 A | 1/1993 | Sarbin et al. |
| 5,197,094 A | 3/1993 | Tillery et al. |
| 5,199,710 A | 4/1993 | Lamle |
| 5,209,476 A | 5/1993 | Eiba |
| 5,224,712 A | 7/1993 | Laughlin et al. |
| 5,240,140 A | 8/1993 | Huen |
| 5,248,142 A | 9/1993 | Breeding |
| 5,257,179 A | 10/1993 | DeMar |
| 5,259,907 A | 11/1993 | Soules et al. |
| 5,261,667 A | 11/1993 | Breeding |
| 5,267,248 A | 11/1993 | Reyner |
| 5,275,411 A | 1/1994 | Breeding |
| 5,276,312 A | 1/1994 | McCarthy |
| 5,283,422 A | 2/1994 | Storch et al. |
| 5,288,081 A | 2/1994 | Breeding |
| 5,299,089 A | 3/1994 | Lwee |
| 5,303,921 A | 4/1994 | Breeding |
| 5,096,197 A | 9/1994 | Embury |
| 5,344,146 A | 9/1994 | Lee |
| 5,356,145 A | 10/1994 | Verschoor |
| 5,362,053 A | 11/1994 | Miller |
| 5,374,061 A | 12/1994 | Albrecht |
| 5,377,973 A | 1/1995 | Jones et al. |
| 5,382,024 A | 1/1995 | Blaha |
| 5,382,025 A | 1/1995 | Sklansky et al. |
| 5,390,910 A | 2/1995 | Mandel et al. |
| 5,397,128 A | 3/1995 | Hesse et al. |
| 5,397,133 A | 3/1995 | Penzias |
| 5,416,308 A | 5/1995 | Hood et al. |
| 5,431,399 A | 7/1995 | Kelley |
| 5,431,407 A | 7/1995 | Hofberg et al. |
| 5,437,462 A | 8/1995 | Breeding |
| 5,445,377 A | 8/1995 | Steinbach |
| 5,470,079 A | 11/1995 | LeStrange et al. |
| D365,853 S | 1/1996 | Zadro |
| 5,489,101 A | 2/1996 | Moody |
| 5,515,477 A | 5/1996 | Sutherland |
| 5,524,888 A | 6/1996 | Heidel |
| 5,531,448 A | 7/1996 | Moody |
| 5,544,892 A | 8/1996 | Breeding |
| 5,575,475 A | 11/1996 | Steinbach |
| 5,584,483 A | 12/1996 | Sines et al. |
| 5,586,766 A | 12/1996 | Forte et al. |
| 5,586,936 A | 12/1996 | Bennett et al. |
| 5,605,334 A | 2/1997 | McCrea, Jr. |
| 5,613,912 A | 3/1997 | Slater |
| 5,632,483 A | 5/1997 | Garczynski et al. |
| 5,636,843 A | 6/1997 | Roberts |
| 5,651,548 A | 7/1997 | French et al. |
| 5,655,961 A | 8/1997 | Acres et al. |
| 5,655,966 A | 8/1997 | Werdin, Jr. et al. |
| 5,669,816 A | 9/1997 | Garczynski et al. |
| 5,676,231 A | 10/1997 | Legras et al. |
| 5,676,372 A | 10/1997 | Sines et al. |
| 5,681,039 A | 10/1997 | Miller |
| 5,683,085 A | 11/1997 | Johnson et al. |
| 5,685,543 A | 11/1997 | Garner |
| 5,690,324 A | 11/1997 | Otomo et al. |
| 5,692,748 A | 12/1997 | Frisco et al. |
| 5,695,189 A | 12/1997 | Breeding et al. |
| 5,701,565 A | 12/1997 | Morgan |
| 5,707,286 A | 1/1998 | Carlson |
| 5,707,287 A | 1/1998 | McCrea, Jr. |
| 5,711,525 A | 1/1998 | Breeding |
| 5,718,427 A | 2/1998 | Cranford et al. |
| 5,719,288 A | 2/1998 | Sens et al. |
| 5,720,484 A | 2/1998 | Hsu |
| 5,722,893 A | 3/1998 | Hill et al. |
| 5,735,525 A | 4/1998 | McCrea, Jr. |
| 5,735,724 A | 4/1998 | Udagawa |
| 5,735,742 A | 4/1998 | French |
| 5,743,798 A | 4/1998 | Adams et al. |
| 5,768,382 A | 6/1998 | Schneier et al. |
| 5,770,533 A | 6/1998 | Franchi |
| 5,770,553 A | 6/1998 | Kroner et al. |
| 5,772,505 A | 6/1998 | Garczynski et al. |
| 5,779,546 A | 7/1998 | Meissner et al. |
| 5,781,647 A | 7/1998 | Fishbine et al. |
| 5,785,321 A | 7/1998 | van Putten et al. |
| 5,788,574 A | 8/1998 | Ornstein et al. |
| 5,791,988 A | 8/1998 | Nomi |
| 5,802,560 A | 9/1998 | Joseph et al. |
| 5,803,808 A | 9/1998 | Strisower |
| 5,810,355 A | 9/1998 | Trilli |
| 5,813,326 A | 9/1998 | Salomon |
| 5,813,912 A | 9/1998 | Shultz |
| 5,814,796 A | 9/1998 | Benson |
| 5,836,775 A | 11/1998 | Hiyama et al. |
| 5,839,730 A | 11/1998 | Pike |
| 5,845,906 A | 12/1998 | Wirth |
| 5,851,011 A | 12/1998 | Lott |
| 5,867,586 A | 2/1999 | Liang |
| 5,879,233 A | 3/1999 | Stupero |
| 5,883,804 A | 3/1999 | Christensen |
| 5,890,717 A | 4/1999 | Rosewarne et al. |
| 5,892,210 A | 4/1999 | Levasseur |
| 5,909,876 A | 6/1999 | Brown |
| 5,911,626 A | 6/1999 | McCrea, Jr. |
| 5,919,090 A | 7/1999 | Mothwurf |
| D412,723 S | 8/1999 | Hachuel et al. |
| 5,936,222 A | 8/1999 | Korsunsky |
| 5,941,769 A | 8/1999 | Order |
| 5,944,310 A | 8/1999 | Johnson et al. |
| D414,527 S | 9/1999 | Tedham |
| 5,957,776 A | 9/1999 | Hoehne |
| 5,974,150 A | 10/1999 | Kaish et al. |
| 5,989,122 A | 11/1999 | Roblejo |
| 5,991,308 A | 11/1999 | Fuhrmann et al. |
| 6,015,311 A | 1/2000 | Benjamin et al. |
| 6,019,368 A | 2/2000 | Sines et al. |
| 6,019,374 A | 2/2000 | Breeding |
| 6,039,650 A | 3/2000 | Hill |
| 6,050,569 A | 4/2000 | Taylor |
| 6,053,695 A | 4/2000 | Longoria et al. |
| 6,061,449 A | 5/2000 | Candelore et al. |
| 6,068,258 A | 5/2000 | Breeding et al. |
| 6,069,564 A | 5/2000 | Hatano et al. |
| 6,071,190 A | 6/2000 | Weiss et al. |
| 6,093,103 A | 7/2000 | McCrea, Jr. |
| 6,113,101 A | 9/2000 | Wirth |
| 6,117,012 A | 9/2000 | McCrea, Jr. |
| D432,588 S | 10/2000 | Tedham |
| 6,126,166 A | 10/2000 | Lorson et al. |
| 6,131,817 A | 10/2000 | Miller |
| 6,139,014 A | 10/2000 | Breeding et al. |
| 6,149,154 A | 11/2000 | Grauzer et al. |
| 6,154,131 A | 11/2000 | Jones, II et al. |

(56) References Cited

U.S. PATENT DOCUMENTS

| | | |
|---|---|---|
| 6,165,069 A | 12/2000 | Sines et al. |
| 6,165,072 A | 12/2000 | Davis et al. |
| 6,183,362 B1 | 2/2001 | Boushy |
| 6,186,895 B1 | 2/2001 | Oliver |
| 6,196,416 B1 | 3/2001 | Seagle |
| 6,200,218 B1 | 3/2001 | Lindsay |
| 6,210,274 B1 | 4/2001 | Carlson |
| 6,213,310 B1 | 4/2001 | Wennersten et al. |
| 6,217,447 B1 | 4/2001 | Lofink et al. |
| 6,234,900 B1 | 5/2001 | Cumbers |
| 6,236,223 B1 | 5/2001 | Brady et al. |
| 6,250,632 B1 | 6/2001 | Albrecht |
| 6,254,002 B1 | 7/2001 | Litman |
| 6,254,096 B1 | 7/2001 | Grauzer et al. |
| 6,254,484 B1 | 7/2001 | McCrea, Jr. |
| 6,257,981 B1 | 7/2001 | Acres et al. |
| 6,267,248 B1 | 7/2001 | Johnson et al. |
| 6,267,648 B1 | 7/2001 | Katayama et al. |
| 6,267,671 B1 | 7/2001 | Hogan |
| 6,270,404 B2 | 8/2001 | Sines et al. |
| 6,272,223 B1 | 8/2001 | Carlson |
| 6,293,546 B1 | 9/2001 | Hessing et al. |
| 6,293,864 B1 | 9/2001 | Romero |
| 6,299,167 B1 | 10/2001 | Sines et al. |
| 6,299,534 B1 | 10/2001 | Breeding et al. |
| 6,299,536 B1 | 10/2001 | Hill |
| 6,308,886 B1 | 10/2001 | Benson et al. |
| 6,313,871 B1 | 11/2001 | Schubert |
| 6,325,373 B1 | 12/2001 | Breeding et al. |
| 6,334,614 B1 | 1/2002 | Breeding |
| 6,341,778 B1 | 1/2002 | Lee |
| 6,342,830 B1 | 1/2002 | Want et al. |
| 6,346,044 B1 | 2/2002 | McCrea, Jr. |
| 6,361,044 B1 | 3/2002 | Block |
| 6,386,973 B1 | 5/2002 | Yoseloff |
| 6,402,142 B1 | 6/2002 | Warren et al. |
| 6,403,908 B2 | 6/2002 | Stardust et al. |
| 6,443,839 B2 | 9/2002 | Stockdale et al. |
| 6,446,864 B1 | 9/2002 | Kim et al. |
| 6,454,266 B1 | 9/2002 | Breeding et al. |
| 6,460,848 B1 | 10/2002 | Soltys et al. |
| 6,464,584 B2 | 10/2002 | Oliver |
| 6,490,277 B1 | 12/2002 | Tzotzkov |
| 6,508,709 B1 | 1/2003 | Karmarkar |
| 6,514,140 B1 | 2/2003 | Storch |
| 6,517,435 B2 | 2/2003 | Soltys et al. |
| 6,517,436 B2 | 2/2003 | Soltys et al. |
| 6,520,857 B2 | 2/2003 | Soltys et al. |
| 6,527,271 B2 | 3/2003 | Soltys et al. |
| 6,530,836 B2 | 3/2003 | Soltys et al. |
| 6,530,837 B2 | 3/2003 | Soltys et al. |
| 6,532,297 B1 | 3/2003 | Lindquist |
| 6,533,276 B2 | 3/2003 | Soltys et al. |
| 6,533,662 B2 | 3/2003 | Soltys et al. |
| 6,561,897 B1 | 5/2003 | Bourbour et al. |
| 6,568,678 B2 | 5/2003 | Breeding et al. |
| 6,579,180 B2 | 6/2003 | Soltys et al. |
| 6,579,181 B2 | 6/2003 | Soltys et al. |
| 6,581,747 B1 | 6/2003 | Charlier et al. |
| 6,582,301 B2 | 6/2003 | Hill |
| 6,582,302 B2 | 6/2003 | Romero |
| 6,585,586 B1 | 7/2003 | Romero |
| 6,585,588 B2 | 7/2003 | Hard |
| 6,585,856 B2 | 7/2003 | Zwick et al. |
| 6,588,750 B1 | 7/2003 | Grauzer et al. |
| 6,588,751 B1 | 7/2003 | Grauzer et al. |
| 6,595,857 B2 | 7/2003 | Soltys et al. |
| 6,609,710 B1 | 8/2003 | Order |
| 6,612,928 B1 | 9/2003 | Bradford et al. |
| 6,616,535 B1 | 9/2003 | Nishizaki et al. |
| 6,619,662 B2 | 9/2003 | Miller |
| 6,622,185 B1 | 9/2003 | Johnson et al. |
| 6,626,757 B2 | 9/2003 | Oliveras |
| 6,629,019 B2 | 9/2003 | Legge et al. |
| 6,629,591 B1 | 10/2003 | Griswold et al. |
| 6,629,889 B2 | 10/2003 | Mothwurf |
| 6,629,894 B1 | 10/2003 | Purton |
| 6,637,622 B1 | 10/2003 | Robinson |
| 6,638,161 B2 | 10/2003 | Soltys et al. |
| 6,645,068 B1 | 11/2003 | Kelly et al. |
| 6,645,077 B2 | 11/2003 | Rowe |
| 6,651,981 B2 | 11/2003 | Grauzer et al. |
| 6,651,982 B2 | 11/2003 | Grauzer et al. |
| 6,651,985 B2 | 11/2003 | Sines et al. |
| 6,652,379 B2 | 11/2003 | Soltys et al. |
| 6,655,684 B2 | 12/2003 | Grauzer et al. |
| 6,655,690 B1 | 12/2003 | Oskwarek |
| 6,658,135 B1 | 12/2003 | Morito et al. |
| 6,659,460 B2 | 12/2003 | Blaha et al. |
| 6,659,461 B2 | 12/2003 | Yoseloff |
| 6,659,875 B2 | 12/2003 | Purton |
| 6,663,490 B2 | 12/2003 | Soltys et al. |
| 6,666,768 B1 | 12/2003 | Akers |
| 6,671,358 B1 | 12/2003 | Seidman et al. |
| 6,676,127 B2 | 1/2004 | Johnson et al. |
| 6,676,517 B2 | 1/2004 | Beavers |
| 6,680,843 B2 | 1/2004 | Farrow et al. |
| 6,685,564 B2 | 2/2004 | Oliver |
| 6,685,567 B2 | 2/2004 | Cockerille et al. |
| 6,685,568 B2 | 2/2004 | Soltys et al. |
| 6,688,597 B2 | 2/2004 | Jones |
| 6,688,979 B2 | 2/2004 | Soltys et al. |
| 6,690,673 B1 | 2/2004 | Jarvis |
| 6,698,756 B1 | 3/2004 | Baker et al. |
| 6,698,759 B2 | 3/2004 | Webb et al. |
| 6,702,289 B1 | 3/2004 | Feola |
| 6,702,290 B2 | 3/2004 | Buono-Correa et al. |
| 6,709,333 B1 | 3/2004 | Bradford et al. |
| 6,712,696 B2 | 3/2004 | Soltys et al. |
| 6,719,288 B2 | 4/2004 | Hessing et al. |
| 6,719,634 B2 | 4/2004 | Mishina et al. |
| 6,722,974 B2 | 4/2004 | Sines et al. |
| 6,726,205 B1 | 4/2004 | Purton |
| 6,732,067 B1 | 5/2004 | Powderly |
| 6,733,012 B2 | 5/2004 | Bui et al. |
| 6,733,388 B2 | 5/2004 | Mothwurf |
| 6,746,333 B1 | 6/2004 | Onda et al. |
| 6,747,560 B2 | 6/2004 | Stevens, III |
| 6,749,510 B2 | 6/2004 | Giobbi |
| 6,758,751 B2 | 7/2004 | Soltys et al. |
| 6,758,757 B2 | 7/2004 | Luciano, Jr. et al. |
| 6,769,693 B2 | 8/2004 | Huard et al. |
| 6,774,782 B2 | 8/2004 | Runyon et al. |
| 6,789,801 B2 | 9/2004 | Snow |
| 6,802,510 B1 | 10/2004 | Haber |
| 6,804,763 B1 | 10/2004 | Stockdale et al. |
| 6,808,173 B2 | 10/2004 | Snow |
| 6,827,282 B2 | 12/2004 | Silverbrook |
| 6,834,251 B1 | 12/2004 | Fletcher |
| 6,840,517 B2 | 1/2005 | Snow et al. |
| 6,842,263 B1 | 1/2005 | Saeki |
| 6,843,725 B2 | 1/2005 | Nelson |
| 6,848,616 B2 | 2/2005 | Tsirline et al. |
| 6,848,844 B2 | 2/2005 | McCue, Jr. et al. |
| 6,848,994 B1 | 2/2005 | Knust et al. |
| 6,857,961 B2 | 2/2005 | Soltys et al. |
| 6,874,784 B1 | 4/2005 | Promutico et al. |
| 6,874,786 B2 | 4/2005 | Bruno |
| 6,877,657 B2 | 4/2005 | Ranard et al. |
| 6,877,748 B1 | 4/2005 | Patroni et al. |
| 6,886,829 B2 | 5/2005 | Hessing et al. |
| 6,889,979 B2 | 5/2005 | Blaha et al. |
| 6,893,347 B1 | 5/2005 | Zilliacus et al. |
| 6,899,628 B2 | 5/2005 | Leen et al. |
| 6,902,167 B2 | 6/2005 | Webb |
| 6,905,121 B1 | 6/2005 | Timpano |
| 6,923,446 B2 | 8/2005 | Snow |
| 6,938,900 B2 | 9/2005 | Snow |
| 6,941,180 B1 | 9/2005 | Fisher et al. |
| 6,950,948 B2 | 9/2005 | Neff |
| 6,955,599 B2 | 10/2005 | Bourbour et al. |
| 6,957,746 B2 | 10/2005 | Martin et al. |
| 6,959,925 B1 | 11/2005 | Baker et al. |
| 6,960,134 B2 | 11/2005 | Hartl et al. |

(56) References Cited

U.S. PATENT DOCUMENTS

| | | |
|---|---|---|
| 6,964,612 B2 | 11/2005 | Soltys et al. |
| 6,986,514 B2 | 1/2006 | Snow |
| 6,988,516 B2 | 1/2006 | Debaes |
| 7,011,309 B2 | 3/2006 | Soltys et al. |
| 7,020,307 B2 | 3/2006 | Hinton et al. |
| 7,028,598 B2 | 4/2006 | Teshima |
| 7,029,009 B2 | 4/2006 | Grauzer et al. |
| 7,036,818 B2 | 5/2006 | Grauzer et al. |
| 7,046,458 B2 | 5/2006 | Nakayama |
| 7,046,764 B1 | 5/2006 | Kump |
| 7,048,629 B2 | 5/2006 | Sines et al. |
| 7,059,602 B2 | 6/2006 | Grauzer et al. |
| 7,066,464 B2 | 6/2006 | Blad et al. |
| 7,068,822 B2 | 6/2006 | Scott |
| 7,073,791 B2 | 7/2006 | Grauzer et al. |
| 7,079,010 B2 | 7/2006 | Champlin |
| 7,084,769 B2 | 8/2006 | Bauer et al. |
| 7,089,420 B1 | 8/2006 | Durst et al. |
| D527,900 S | 9/2006 | Dewa |
| 7,106,201 B2 | 9/2006 | Tuttle |
| 7,113,094 B2 | 9/2006 | Garber et al. |
| 7,114,718 B2 | 10/2006 | Grauzer et al. |
| 7,124,947 B2 | 10/2006 | Storch |
| 7,128,652 B1 | 10/2006 | Lavoie et al. |
| 7,137,627 B2 | 11/2006 | Grauzer et al. |
| 7,139,108 B2 | 11/2006 | Andersen et al. |
| 7,140,614 B2 | 11/2006 | Snow |
| 7,162,035 B1 | 1/2007 | Durst et al. |
| 7,165,769 B2 | 1/2007 | Crenshaw et al. |
| 7,165,770 B2 | 1/2007 | Snow |
| 7,175,522 B2 | 2/2007 | Hartl |
| 7,186,181 B2 | 3/2007 | Rowe |
| 7,201,656 B2 | 4/2007 | Darder |
| 7,202,888 B2 | 4/2007 | Tecu et al. |
| 7,203,841 B2 | 4/2007 | Jackson et al. |
| 7,213,812 B2 | 5/2007 | Schubert |
| 7,222,852 B2 | 5/2007 | Soltys |
| 7,222,855 B2 | 5/2007 | Sorge |
| 7,231,812 B1 | 6/2007 | Lagare |
| 7,234,698 B2 | 6/2007 | Grauzer et al. |
| 7,237,969 B2 | 7/2007 | Bartman |
| 7,243,148 B2 | 7/2007 | Keir et al. |
| 7,243,698 B2 | 7/2007 | Siegel |
| 7,246,799 B2 | 7/2007 | Snow |
| 7,255,344 B2 | 8/2007 | Grauzer et al. |
| 7,255,351 B2 | 8/2007 | Yoseloff et al. |
| 7,255,642 B2 | 8/2007 | Sines et al. |
| 7,257,630 B2 | 8/2007 | Cole et al. |
| 7,261,294 B2 | 8/2007 | Grauzer et al. |
| 7,264,241 B2 | 9/2007 | Schubert et al. |
| 7,264,243 B2 | 9/2007 | Yoseloff et al. |
| 7,277,570 B2 | 10/2007 | Armstrong |
| 7,278,923 B2 | 10/2007 | Grauzer et al. |
| 7,294,056 B2 | 11/2007 | Lowell et al. |
| 7,297,062 B2 | 11/2007 | Gatto et al. |
| 7,300,056 B2 | 11/2007 | Gioia et al. |
| 7,303,473 B2 | 12/2007 | Rowe |
| 7,303,475 B2 | 12/2007 | Britt et al. |
| 7,309,065 B2 | 12/2007 | Yoseloff et al. |
| 7,316,609 B2 | 1/2008 | Dunn et al. |
| 7,316,615 B2 | 1/2008 | Soltys et al. |
| 7,322,576 B2 | 1/2008 | Grauzer et al. |
| 7,331,579 B2 | 2/2008 | Snow |
| 7,334,794 B2 | 2/2008 | Snow |
| 7,338,044 B2 | 3/2008 | Grauzer et al. |
| 7,338,362 B1 | 3/2008 | Gallagher |
| 7,341,510 B2 | 3/2008 | Bourbour et al. |
| D566,784 S | 4/2008 | Palmer |
| 7,357,321 B2 | 4/2008 | Yoshida |
| 7,360,094 B2 | 4/2008 | Neff |
| 7,367,561 B2 | 5/2008 | Blaha et al. |
| 7,367,563 B2 | 5/2008 | Yoseloff et al. |
| 7,367,565 B2 | 5/2008 | Chiu |
| 7,367,884 B2 | 5/2008 | Breeding et al. |
| 7,374,170 B2 | 5/2008 | Grauzer et al. |
| 7,384,044 B2 | 6/2008 | Grauzer et al. |
| 7,387,300 B2 | 6/2008 | Snow |
| 7,389,990 B2 | 6/2008 | Mourad |
| 7,390,256 B2 | 6/2008 | Soltys et al. |
| 7,399,226 B2 | 7/2008 | Mishra |
| 7,407,438 B2 | 8/2008 | Schubert et al. |
| 7,413,191 B2 | 8/2008 | Grauzer et al. |
| 7,434,805 B2 | 10/2008 | Grauzer et al. |
| 7,436,957 B1 | 10/2008 | Fisher et al. |
| 7,448,626 B2 | 11/2008 | Fleckenstein |
| 7,458,582 B2 | 12/2008 | Snow et al. |
| 7,461,843 B1 | 12/2008 | Baker et al. |
| 7,464,932 B2 | 12/2008 | Darling |
| 7,464,934 B2 | 12/2008 | Schwartz |
| 7,472,906 B2 | 1/2009 | Shai |
| 7,478,813 B1 | 1/2009 | Hofferber et al. |
| 7,500,672 B2 | 3/2009 | Ho |
| 7,506,874 B2 | 3/2009 | Hall |
| 7,510,186 B2 | 3/2009 | Fleckenstein |
| 7,510,190 B2 | 3/2009 | Snow et al. |
| 7,510,194 B2 | 3/2009 | Soltys et al. |
| 7,510,478 B2 | 3/2009 | Benbrahim et al. |
| 7,513,437 B2 | 4/2009 | Douglas |
| 7,515,718 B2 | 4/2009 | Nguyen et al. |
| 7,523,935 B2 | 4/2009 | Grauzer et al. |
| 7,523,936 B2 | 4/2009 | Grauzer et al. |
| 7,523,937 B2 | 4/2009 | Fleckenstein |
| 7,525,510 B2 | 4/2009 | Beland et al. |
| 7,537,216 B2 | 5/2009 | Soltys et al. |
| 7,540,497 B2 | 6/2009 | Tseng |
| 7,540,498 B2 | 6/2009 | Crenshaw et al. |
| 7,549,643 B2 | 6/2009 | Quach |
| 7,554,753 B2 | 6/2009 | Wakamiya |
| 7,556,197 B2 | 7/2009 | Yoshida |
| 7,556,266 B2 | 7/2009 | Blaha et al. |
| 7,575,237 B2 | 8/2009 | Snow |
| 7,578,506 B2 | 8/2009 | Lambert |
| 7,584,962 B2 | 9/2009 | Breeding et al. |
| 7,584,963 B2 | 9/2009 | Krenn et al. |
| 7,584,966 B2 | 9/2009 | Snow |
| 7,591,728 B2 | 9/2009 | Gioia et al. |
| 7,593,544 B2 | 9/2009 | Downs |
| 7,594,660 B2 | 9/2009 | Baker et al. |
| 7,597,623 B2 | 10/2009 | Grauzer et al. |
| 7,644,923 B1 | 1/2010 | Dickinson et al. |
| 7,661,676 B2 | 2/2010 | Smith et al. |
| 7,666,090 B2 | 2/2010 | Hettinger |
| 7,669,852 B2 | 3/2010 | Baker et al. |
| 7,669,853 B2 | 3/2010 | Jones |
| 7,677,565 B2 | 3/2010 | Grauzer et al. |
| 7,677,566 B2 | 3/2010 | Krenn et al. |
| 7,686,681 B2 | 3/2010 | Soltys et al. |
| 7,699,694 B2 | 4/2010 | Hill |
| 7,735,657 B2 | 6/2010 | Johnson |
| 7,740,244 B2 | 6/2010 | Ho |
| 7,744,452 B2 | 6/2010 | Cimring et al. |
| 7,753,373 B2 | 7/2010 | Grauzer et al. |
| 7,753,374 B2 | 7/2010 | Ho |
| 7,753,798 B2 | 7/2010 | Soltys |
| 7,758,425 B2 | 7/2010 | Poh et al. |
| 7,762,554 B2 | 7/2010 | Ho |
| 7,764,836 B2 | 7/2010 | Downs et al. |
| 7,766,332 B2 | 8/2010 | Grauzer et al. |
| 7,766,333 B1 | 8/2010 | Stardust |
| 7,769,232 B2 | 8/2010 | Downs, III |
| 7,769,853 B2 | 8/2010 | Nezamzadeh |
| 7,773,749 B1 | 8/2010 | Durst et al. |
| 7,780,529 B2 | 8/2010 | Rowe et al. |
| 7,784,790 B2 | 8/2010 | Grauzer et al. |
| 7,804,982 B2 | 9/2010 | Howard et al. |
| 7,824,255 B2 | 11/2010 | Lutnick |
| 7,846,020 B2 | 12/2010 | Walker et al. |
| 7,867,080 B2 | 1/2011 | Nicely et al. |
| 7,890,365 B2 | 2/2011 | Hettinger |
| 7,900,923 B2 | 3/2011 | Toyama et al. |
| 7,901,285 B2 | 3/2011 | Tran et al. |
| 7,908,169 B2 | 3/2011 | Hettinger |
| 7,909,689 B2 | 3/2011 | Lardie |
| 7,933,448 B2 | 4/2011 | Downs, III |

(56) References Cited

U.S. PATENT DOCUMENTS

| | | |
|---|---|---|
| 7,946,586 B2 | 5/2011 | Krenn et al. |
| 7,967,294 B2 | 6/2011 | Blaha et al. |
| 7,976,023 B1 | 7/2011 | Hessing et al. |
| 7,931,533 B2 | 8/2011 | LeMay et al. |
| 7,988,152 B2 | 8/2011 | Sines et al. |
| 7,988,554 B2 | 8/2011 | LeMay et al. |
| 7,995,196 B1 | 8/2011 | Fraser |
| 8,002,638 B2 | 8/2011 | Grauzer et al. |
| 8,011,661 B2 | 9/2011 | Stasson |
| 8,016,663 B2 | 9/2011 | Soltys et al. |
| 8,021,231 B2 | 9/2011 | Walker et al. |
| 8,025,294 B2 | 9/2011 | Grauzer et al. |
| 8,038,521 B2 | 10/2011 | Grauzer et al. |
| RE42,944 E | 11/2011 | Blaha et al. |
| 8,057,302 B2 | 11/2011 | Wells et al. |
| 8,062,134 B2 | 11/2011 | Kelly et al. |
| 8,070,574 B2 | 12/2011 | Grauzer et al. |
| 8,092,307 B2 | 1/2012 | Kelly |
| 8,092,309 B2 | 1/2012 | Bickley |
| 8,109,514 B2 | 2/2012 | Toyama |
| 8,141,875 B2 | 3/2012 | Grauzer et al. |
| 8,150,158 B2 | 4/2012 | Downs, III |
| 8,171,567 B1 | 5/2012 | Fraser et al. |
| 8,210,536 B2 | 7/2012 | Blaha et al. |
| 8,221,244 B2 | 7/2012 | French |
| 8,251,293 B2 | 8/2012 | Nagata et al. |
| 8,267,404 B2 | 9/2012 | Grauzer et al. |
| 8,270,603 B1 | 9/2012 | Durst et al. |
| 8,287,347 B2 | 10/2012 | Snow et al. |
| 8,287,386 B2 | 10/2012 | Miller et al. |
| 8,319,666 B2 | 11/2012 | Weinmann et al. |
| 8,337,296 B2 | 12/2012 | Grauzer et al. |
| 8,342,525 B2 | 1/2013 | Scheper et al. |
| 8,342,526 B1 | 1/2013 | Sampson |
| 8,342,529 B2 | 1/2013 | Snow |
| 8,353,513 B2 | 1/2013 | Swanson |
| 8,381,918 B2 | 2/2013 | Johnson |
| 8,419,521 B2 | 4/2013 | Grauzer et al. |
| 8,429,229 B2 | 4/2013 | Sepich et al. |
| 8,444,147 B2 | 5/2013 | Grauzer et al. |
| 8,444,489 B2 | 5/2013 | Lian et al. |
| 8,469,360 B2 | 6/2013 | Sines |
| 8,475,252 B2 | 7/2013 | Savage et al. |
| 8,480,088 B2 | 7/2013 | Toyama et al. |
| 8,485,527 B2 | 7/2013 | Sampson et al. |
| 8,490,973 B2 | 7/2013 | Yoseloff et al. |
| 8,498,444 B2 | 7/2013 | Sharma |
| 8,505,916 B2 | 8/2013 | Grauzer et al. |
| 8,511,684 B2 | 8/2013 | Grauzer et al. |
| 8,512,146 B2 | 8/2013 | Gururajan et al. |
| 8,550,464 B2 | 10/2013 | Soltys et al. |
| 8,556,263 B2 | 10/2013 | Grauzer et al. |
| 8,579,289 B2 | 11/2013 | Rynda et al. |
| 8,602,416 B2 | 12/2013 | Toyama |
| 8,616,552 B2 | 12/2013 | Czyzewski et al. |
| 8,628,086 B2 | 1/2014 | Krenn et al. |
| 8,651,485 B2 | 2/2014 | Stasson |
| 8,662,500 B2 | 3/2014 | Swanson |
| 8,695,978 B1 | 4/2014 | Ho |
| 8,702,100 B2 | 4/2014 | Snow et al. |
| 8,702,101 B2 | 4/2014 | Scheper et al. |
| 8,720,891 B2 | 5/2014 | Hessing et al. |
| 8,758,111 B2 | 6/2014 | Lutnick |
| 8,777,710 B2 | 7/2014 | Grauzer et al. |
| 8,820,745 B2 | 9/2014 | Grauzer et al. |
| 8,844,930 B2 | 9/2014 | Sampson |
| 8,899,587 B2 | 12/2014 | Grauzer et al. |
| 8,919,775 B2 | 12/2014 | Wadds et al. |
| 9,101,821 B2 | 8/2015 | Snow |
| 9,251,661 B2 | 2/2016 | Tammesoo |
| 9,266,012 B2 | 2/2016 | Grauzer |
| 9,280,866 B2 | 3/2016 | Nayak et al. |
| 2001/0036231 A1 | 11/2001 | Easwar et al. |
| 2001/0036866 A1 | 11/2001 | Stockdale et al. |
| 2002/0017481 A1 | 2/2002 | Johnson et al. |
| 2002/0045478 A1 | 4/2002 | Soltys et al. |
| 2002/0045481 A1 | 4/2002 | Soltys et al. |
| 2002/0063389 A1 | 5/2002 | Breeding et al. |
| 2002/0068635 A1 | 6/2002 | Hill |
| 2002/0070499 A1 | 6/2002 | Breeding et al. |
| 2002/0094869 A1 | 7/2002 | Harkham |
| 2002/0107067 A1 | 8/2002 | McGlone et al. |
| 2002/0107072 A1 | 8/2002 | Giobbi |
| 2002/0113368 A1 | 8/2002 | Hessing et al. |
| 2002/0135692 A1 | 9/2002 | Fujinawa |
| 2002/0142820 A1 | 10/2002 | Bartlett |
| 2002/0163122 A1 | 11/2002 | Vancura |
| 2002/0163125 A1 | 11/2002 | Grauzer et al. |
| 2002/0187821 A1 | 12/2002 | Soltys et al. |
| 2002/0187830 A1 | 12/2002 | Stockdale et al. |
| 2003/0003997 A1 | 1/2003 | Vuong et al. |
| 2003/0007143 A1 | 1/2003 | McArthur et al. |
| 2003/0042673 A1 | 3/2003 | Grauzer |
| 2003/0047870 A1 | 3/2003 | Blaha et al. |
| 2003/0048476 A1 | 3/2003 | Yamakawa |
| 2003/0052449 A1 | 3/2003 | Grauzer et al. |
| 2003/0052450 A1 | 3/2003 | Grauzer et al. |
| 2003/0064798 A1 | 4/2003 | Grauzer et al. |
| 2003/0067112 A1 | 4/2003 | Grauzer et al. |
| 2003/0071413 A1 | 4/2003 | Blaha et al. |
| 2003/0073498 A1 | 4/2003 | Grauzer et al. |
| 2003/0075865 A1 | 4/2003 | Grauzer et al. |
| 2003/0075866 A1 | 4/2003 | Blaha et al. |
| 2003/0087694 A1 | 5/2003 | Storch |
| 2003/0090059 A1 | 5/2003 | Grauzer et al. |
| 2003/0094756 A1 | 5/2003 | Grauzer et al. |
| 2003/0151194 A1 | 8/2003 | Hessing et al. |
| 2003/0195025 A1 | 10/2003 | Hill |
| 2004/0015423 A1 | 1/2004 | Walker et al. |
| 2004/0036214 A1 | 2/2004 | Baker et al. |
| 2004/0067789 A1 | 4/2004 | Grauzer et al. |
| 2004/0100026 A1 | 5/2004 | Haggard |
| 2004/0108654 A1 | 6/2004 | Grauzer et al. |
| 2004/0116179 A1 | 6/2004 | Nicely et al. |
| 2004/0169332 A1 | 9/2004 | Grauzer et al. |
| 2004/0180722 A1 | 9/2004 | Giobbi |
| 2004/0224777 A1 | 11/2004 | Smith et al. |
| 2004/0245720 A1 | 12/2004 | Grauzer et al. |
| 2004/0259618 A1 | 12/2004 | Soltys et al. |
| 2005/0012671 A1 | 1/2005 | Bisig |
| 2005/0023752 A1 | 2/2005 | Grauzer et al. |
| 2005/0026680 A1 | 2/2005 | Gururajan |
| 2005/0035548 A1 | 2/2005 | Yoseloff |
| 2005/0037843 A1 | 2/2005 | Wells et al. |
| 2005/0040594 A1 | 2/2005 | Krenn et al. |
| 2005/0051955 A1 | 3/2005 | Schubert et al. |
| 2005/0051956 A1 | 3/2005 | Grauzer et al. |
| 2005/0062227 A1 | 3/2005 | Grauzer et al. |
| 2005/0062228 A1 | 3/2005 | Grauzer et al. |
| 2005/0062229 A1 | 3/2005 | Grauzer et al. |
| 2005/0082750 A1 | 4/2005 | Grauzer et al. |
| 2005/0093231 A1 | 5/2005 | Grauzer et al. |
| 2005/0104289 A1 | 5/2005 | Grauzer et al. |
| 2005/0104290 A1 | 5/2005 | Grauzer et al. |
| 2005/0110210 A1 | 5/2005 | Soltys et al. |
| 2005/0113166 A1 | 5/2005 | Grauzer et al. |
| 2005/0113171 A1 | 5/2005 | Hodgson |
| 2005/0119048 A1 | 6/2005 | Soltys |
| 2005/0121852 A1 | 6/2005 | Soltys et al. |
| 2005/0137005 A1 | 6/2005 | Soltys et al. |
| 2005/0140090 A1 | 6/2005 | Breeding et al. |
| 2005/0146093 A1 | 7/2005 | Grauzer et al. |
| 2005/0148391 A1 | 7/2005 | Tain |
| 2005/0164759 A1 | 7/2005 | Smith et al. |
| 2005/0192092 A1 | 9/2005 | Breckner et al. |
| 2005/0206077 A1 | 9/2005 | Grauzer et al. |
| 2002/0155869 A1 | 10/2005 | Soltys et al. |
| 2005/0242500 A1 | 11/2005 | Downs |
| 2005/0272501 A1 | 12/2005 | Tran et al. |
| 2005/0288083 A1 | 12/2005 | Downs |
| 2005/0288086 A1 | 12/2005 | Schubert et al. |
| 2006/0027970 A1 | 2/2006 | Kyrychenko |
| 2006/0033269 A1 | 2/2006 | Grauzer et al. |
| 2006/0033270 A1 | 2/2006 | Grauzer et al. |

(56) References Cited

U.S. PATENT DOCUMENTS

| | | |
|---|---|---|
| 2006/0046853 A1 | 3/2006 | Black |
| 2006/0063577 A1 | 3/2006 | Downs, III et al. |
| 2006/0066048 A1 | 3/2006 | Krenn et al. |
| 2006/0181022 A1 | 8/2006 | Grauzer et al. |
| 2006/0183540 A1 | 8/2006 | Grauzer et al. |
| 2006/0189381 A1 | 8/2006 | Daniel et al. |
| 2006/0199649 A1 | 9/2006 | Soltys et al. |
| 2006/0205508 A1 | 9/2006 | Green |
| 2006/0220312 A1 | 10/2006 | Baker et al. |
| 2006/0220313 A1 | 10/2006 | Baker et al. |
| 2006/0252521 A1 | 11/2006 | Gururajan et al. |
| 2006/0252554 A1 | 11/2006 | Gururajan et al. |
| 2006/0279040 A1 | 12/2006 | Downs et al. |
| 2006/0281534 A1 | 12/2006 | Grauzer et al. |
| 2007/0001395 A1 | 1/2007 | Gioia et al. |
| 2007/0006708 A1 | 1/2007 | Laakso |
| 2007/0015583 A1 | 1/2007 | Tran |
| 2007/0018389 A1 | 1/2007 | Downs, III |
| 2007/0045959 A1 | 3/2007 | Soltys |
| 2007/0049368 A1 | 3/2007 | Kuhn et al. |
| 2007/0057454 A1 | 3/2007 | Fleckenstein |
| 2007/0057469 A1 | 3/2007 | Grauzer et al. |
| 2007/0066387 A1 | 3/2007 | Matsuno et al. |
| 2007/0069462 A1 | 3/2007 | Downs, III et al. |
| 2007/0072677 A1 | 3/2007 | Lavoie et al. |
| 2007/0102879 A1 | 5/2007 | Stasson |
| 2007/0111773 A1 | 5/2007 | Gururajan et al. |
| 2007/0184905 A1 | 8/2007 | Gatto et al. |
| 2007/0197294 A1 | 8/2007 | Gong |
| 2007/0197298 A1 | 8/2007 | Rowe |
| 2007/0202941 A1 | 8/2007 | Miltenberger et al. |
| 2007/0222147 A1 | 9/2007 | Blaha et al. |
| 2007/0225055 A1 | 9/2007 | Weisman |
| 2007/0233567 A1 | 10/2007 | Daly |
| 2007/0238506 A1 | 10/2007 | Ruckle |
| 2007/0259709 A1 | 11/2007 | Kelly et al. |
| 2007/0267812 A1 | 11/2007 | Grauzer et al. |
| 2007/0272600 A1 | 11/2007 | Johnson |
| 2007/0278739 A1 | 12/2007 | Swanson |
| 2007/0287534 A1* | 12/2007 | Fleckenstein ............ A63F 1/12 463/29 |
| 2007/0290438 A1 | 12/2007 | Grauzer et al. |
| 2007/0298865 A1 | 12/2007 | Soltys |
| 2008/0006997 A1 | 1/2008 | Scheper et al. |
| 2008/0006998 A1 | 1/2008 | Grauzer et al. |
| 2008/0022415 A1 | 1/2008 | Kuo et al. |
| 2008/0032763 A1 | 2/2008 | Giobbi |
| 2008/0039192 A1 | 2/2008 | Laut |
| 2008/0039208 A1 | 2/2008 | Abrink et al. |
| 2008/0096656 A1 | 4/2008 | LeMay et al. |
| 2008/0111300 A1 | 5/2008 | Czyzewski et al. |
| 2008/0113700 A1 | 5/2008 | Czyzewski et al. |
| 2008/0113783 A1 | 5/2008 | Czyzewski et al. |
| 2008/0136108 A1 | 6/2008 | Polay |
| 2008/0143048 A1 | 6/2008 | Shigeta |
| 2008/0176627 A1 | 7/2008 | Lardie |
| 2008/0217218 A1 | 9/2008 | Johnson |
| 2008/0234046 A1 | 9/2008 | Kinsley |
| 2008/0234047 A1 | 9/2008 | Nguyen |
| 2008/0248875 A1 | 10/2008 | Beatty |
| 2008/0284096 A1 | 11/2008 | Toyama et al. |
| 2008/0303210 A1 | 12/2008 | Grauzer et al. |
| 2008/0315517 A1 | 12/2008 | Toyama et al. |
| 2009/0026700 A2 | 1/2009 | Shigeta |
| 2009/0048026 A1 | 2/2009 | French |
| 2009/0054161 A1 | 2/2009 | Schuber et al. |
| 2009/0072477 A1 | 3/2009 | Tseng et al. |
| 2009/0121429 A1 | 3/2009 | Walsh et al. |
| 2009/0091078 A1 | 4/2009 | Grauzer et al. |
| 2009/0100409 A1 | 4/2009 | Toneguzzo |
| 2009/0104963 A1 | 4/2009 | Burman |
| 2009/0140492 A1 | 6/2009 | Yoseloff et al. |
| 2009/0166970 A1 | 7/2009 | Rosh et al. |
| 2009/0176547 A1 | 7/2009 | Katz |
| 2009/0179378 A1 | 7/2009 | Amaitis et al. |
| 2009/0186676 A1 | 7/2009 | Amaitis et al. |
| 2009/0189346 A1 | 7/2009 | Krenn et al. |
| 2009/0191933 A1 | 7/2009 | French |
| 2009/0194988 A1 | 8/2009 | Wright et al. |
| 2009/0197662 A1 | 8/2009 | Wright et al. |
| 2009/0224476 A1 | 9/2009 | Grauzer et al. |
| 2009/0227318 A1 | 9/2009 | Wright et al. |
| 2009/0227360 A1 | 9/2009 | Gioia et al. |
| 2009/0250873 A1 | 10/2009 | Jones |
| 2009/0253478 A1 | 10/2009 | Walker et al. |
| 2009/0253503 A1 | 10/2009 | Krise et al. |
| 2009/0267296 A1 | 10/2009 | Ho et al. |
| 2009/0267297 A1 | 10/2009 | Blaha et al. |
| 2009/0283969 A1 | 11/2009 | Tseng et al. |
| 2009/0298577 A1 | 12/2009 | Gagner et al. |
| 2009/0302535 A1 | 12/2009 | Ho et al. |
| 2009/0302537 A1 | 12/2009 | Ho et al. |
| 2009/0312093 A1 | 12/2009 | Walker et al. |
| 2009/0314188 A1 | 12/2009 | Toyama et al. |
| 2010/0013152 A1 | 1/2010 | Grauzer |
| 2010/0038849 A1 | 2/2010 | Scheper et al. |
| 2010/0048304 A1 | 2/2010 | Boesen |
| 2010/0069155 A1 | 3/2010 | Schwartz et al. |
| 2010/0178987 A1 | 7/2010 | Pacey |
| 2010/0197410 A1 | 8/2010 | Leen et al. |
| 2010/0234110 A1 | 9/2010 | Clarkson |
| 2010/0240440 A1 | 9/2010 | Szrek et al. |
| 2010/0244376 A1 | 9/2010 | Johnson |
| 2010/0244382 A1 | 9/2010 | Snow |
| 2010/0252992 A1 | 10/2010 | Sines |
| 2010/0255899 A1 | 10/2010 | Paulsen |
| 2010/0276880 A1 | 11/2010 | Grauzer et al. |
| 2010/0311493 A1 | 12/2010 | Miller et al. |
| 2010/0311494 A1 | 12/2010 | Miller et al. |
| 2010/0314830 A1 | 12/2010 | Grauzer et al. |
| 2010/0320685 A1 | 12/2010 | Grauzer |
| 2011/0006480 A1 | 1/2011 | Grauzer |
| 2011/0012303 A1 | 1/2011 | Kourgiantakis et al. |
| 2011/0024981 A1 | 2/2011 | Tseng |
| 2011/0052049 A1 | 3/2011 | Rajaraman et al. |
| 2011/0062662 A1 | 3/2011 | Ohta |
| 2011/0078096 A1 | 3/2011 | Bounds |
| 2011/0079959 A1 | 4/2011 | Hartley |
| 2011/0105208 A1 | 5/2011 | Bickley |
| 2011/0109042 A1 | 5/2011 | Rynda |
| 2011/0130185 A1 | 6/2011 | Walker |
| 2011/0130190 A1 | 6/2011 | Hamman et al. |
| 2011/0159952 A1 | 6/2011 | Kerr |
| 2011/0159953 A1 | 6/2011 | Kerr |
| 2011/0165936 A1 | 7/2011 | Kerr |
| 2011/0172008 A1 | 7/2011 | Alderucci |
| 2011/0183748 A1 | 7/2011 | Wilson et al. |
| 2011/0230268 A1 | 9/2011 | Williams |
| 2011/0269529 A1 | 11/2011 | Baerlocher |
| 2011/0272881 A1 | 11/2011 | Sines |
| 2011/0285081 A1 | 11/2011 | Stasson |
| 2011/0287829 A1 | 11/2011 | Clarkson et al. |
| 2012/0015724 A1 | 1/2012 | Ocko et al. |
| 2012/0015725 A1 | 1/2012 | Ocko et al. |
| 2012/0015743 A1 | 1/2012 | Lam et al. |
| 2012/0015747 A1 | 1/2012 | Ocko et al. |
| 2012/0021835 A1 | 1/2012 | Keller et al. |
| 2012/0034977 A1 | 2/2012 | Kammler |
| 2012/0062745 A1 | 3/2012 | Han et al. |
| 2012/0074646 A1 | 3/2012 | Grauzer et al. |
| 2012/0091656 A1 | 4/2012 | Blaha et al. |
| 2012/0095982 A1 | 4/2012 | Lennington et al. |
| 2012/0161393 A1 | 6/2012 | Krenn et al. |
| 2012/0175841 A1 | 7/2012 | Grauzer |
| 2012/0181747 A1 | 7/2012 | Grauzer et al. |
| 2012/0187625 A1 | 7/2012 | Downs, III et al. |
| 2012/0242782 A1 | 9/2012 | Huang |
| 2012/0286471 A1 | 11/2012 | Grauzer et al. |
| 2012/0306152 A1 | 12/2012 | Krishnamurty et al. |
| 2013/0020761 A1 | 1/2013 | Sines et al. |
| 2013/0023318 A1 | 1/2013 | Abrahamson |
| 2013/0085638 A1 | 4/2013 | Weinmann et al. |
| 2013/0099448 A1 | 4/2013 | Scheper et al. |
| 2013/0109455 A1 | 5/2013 | Grauzer et al. |

(56) References Cited

U.S. PATENT DOCUMENTS

| | | |
|---|---|---|
| 2013/0132306 A1 | 5/2013 | Kami et al. |
| 2013/0147116 A1 | 6/2013 | Stasson |
| 2013/0161905 A1 | 6/2013 | Grauzer et al. |
| 2013/0228972 A1 | 9/2013 | Grauzer et al. |
| 2013/0300059 A1 | 11/2013 | Sampson et al. |
| 2013/0337922 A1 | 12/2013 | Kuhn |
| 2014/0027979 A1 | 1/2014 | Stasson et al. |
| 2014/0094239 A1 | 4/2014 | Grauzer et al. |
| 2014/0103606 A1 | 4/2014 | Grauzer et al. |
| 2014/0138907 A1 | 5/2014 | Rynda et al. |
| 2014/0145399 A1 | 5/2014 | Krenn et al. |
| 2014/0171170 A1 | 6/2014 | Krishnamurty et al. |
| 2014/0175724 A1 | 6/2014 | Huhtala et al. |
| 2014/0183818 A1 | 7/2014 | Czyzewski et al. |
| 2015/0021242 A1* | 1/2015 | Johnson .............. A63F 1/12 209/552 |
| 2015/0069699 A1* | 3/2015 | Blazevic .............. A63F 1/12 273/149 R |
| 2015/0196834 A1 | 7/2015 | Snow |

FOREIGN PATENT DOCUMENTS

| | | |
|---|---|---|
| AU | 697805 B2 | 10/1998 |
| AU | 757636 B2 | 2/2003 |
| CA | 2266555 A1 | 9/1996 |
| CA | 2284017 A1 | 9/1998 |
| CA | 2612138 A1 | 12/2006 |
| CN | 2051521 U | 1/1990 |
| CN | 2848303 Y | 12/2006 |
| CN | 2855481 Y | 1/2007 |
| CN | 1933881 A | 3/2007 |
| CN | 2877425 Y | 3/2007 |
| CN | 200954370 Y | 10/2007 |
| CN | 200987893 Y | 12/2007 |
| CN | 101099896 A | 1/2008 |
| CN | 101127131 A | 2/2008 |
| CN | 201085907 Y | 7/2008 |
| CN | 201139926 Y | 10/2008 |
| CN | 100571826 C | 12/2009 |
| CN | 1771077 B | 6/2010 |
| CN | 101783011 B | 12/2011 |
| CN | 202724641 U | 2/2013 |
| CN | 202983149 U | 6/2013 |
| CZ | 24952 U1 | 2/2013 |
| DE | 2816377 A1 | 10/1979 |
| DE | 3807127 A1 | 9/1989 |
| DE | 2757341 A1 | 9/1998 |
| EP | 0777514 B1 | 2/2000 |
| EP | 1502631 A1 | 2/2005 |
| EP | 1713026 A1 | 10/2006 |
| EP | 1194888 A1 | 8/2009 |
| EP | 2228106 A1 | 9/2010 |
| EP | 1575261 B1 | 8/2012 |
| FR | 2375918 A1 | 7/1978 |
| GB | 289552 A | 4/1928 |
| GB | 337147 A | 9/1929 |
| GB | 414014 A | 7/1934 |
| GB | 672616 A | 5/1952 |
| JP | 10063933 A | 3/1998 |
| JP | 11045321 A | 2/1999 |
| JP | 2000251031 A | 9/2000 |
| JP | 2001327647 A | 11/2001 |
| JP | 2002165916 A | 6/2002 |
| JP | 2003250950 A | 9/2003 |
| JP | 2005198668 A | 7/2005 |
| JP | 2008246061 A | 10/2008 |
| NO | 9840136 A1 | 4/1998 |
| TW | M335308 U | 7/2008 |
| TW | M359356 U | 6/2009 |
| WO | 8700764 A1 | 2/1987 |
| WO | 9221413 A1 | 12/1992 |
| WO | 9528210 A1 | 10/1995 |
| WO | 9607153 A1 | 3/1996 |
| WO | 9710577 A1 | 3/1997 |
| WO | 9814249 A1 | 9/1998 |
| WO | 9943404 A1 | 9/1999 |
| WO | 9952610 A1 | 10/1999 |
| WO | 9952611 A1 | 10/1999 |
| WO | 200051076 A1 | 8/2000 |
| WO | 156670 A1 | 8/2001 |
| WO | 178854 A3 | 10/2001 |
| WO | 205914 A1 | 1/2002 |
| WO | 3026763 A1 | 4/2003 |
| WO | 2004067889 A1 | 12/2004 |
| WO | 2004112923 A1 | 12/2004 |
| WO | 2006031472 A2 | 3/2006 |
| WO | 2006039308 A2 | 4/2006 |
| WO | 03004116 A1 | 11/2007 |
| WO | 2008005286 A2 | 1/2008 |
| WO | 2008006023 A2 | 1/2008 |
| WO | 2008091809 A2 | 7/2008 |
| WO | 2009137541 A2 | 11/2009 |
| WO | 2010001032 A2 | 1/2010 |
| WO | 2010052573 A2 | 5/2010 |
| WO | 2010055328 A2 | 5/2010 |
| WO | 2010117446 A2 | 10/2010 |
| WO | 2013019677 A2 | 2/2013 |

OTHER PUBLICATIONS

European Patent Application Search Report—European Patent Application No. 06772987.1, dated Dec. 10, 2009, 5 pages.
European Examination Report for European Application No. 02 780 410, dated Jan. 25, 2010, 5 pages.
European Examination Report for European Application No. 02 780 410, dated Aug. 9, 2011, 4 pages.
Fine, Randall A., "Talking Tables", dated Apr. 25, 2012. Global Gaming Business Magazine, vol. 11, No. 5, May 2012. Retrieved on Oct. 3, 2016 from the Internet: <URL: https://ggbmagazine.com/issue/vol-11-no-5-may-2012/article/talking-tables> (4 pages).
Genevieve Orr, CS-449: Neural Networks Willamette University, http://www.willamette.edu/~gorr/classes/cs449/intro.html (4 pages), Fall 1999.
http://www.google.com/search?tbm=pts &q=Card+handling+devicve+with+input+and+outpu.. Jun. 8, 2012.
http://www.ildado.com/casino_glossary.html, Feb. 1, 2001, pp. 1-8.
https://web.archive.org/web/19991004000323/http://travelwizardtravel.com/majon.htm, Oct. 4, 1999, 2 pages.
http://www.google.com/search?tbm=pts &q=shuffling+zone+onOopposite+site+of+input+ . . . Jul. 18, 2012.
Litwiller, Dave, CCD vs. CMOS: Facts and Fiction reprinted from Jan. 2001 Issue of Photonics Spectra, Laurin Publishing Co. Inc. (4 pages).
Malaysian Patent Application Substantive Examination Adverse Report—Malaysian Patent Application Serial No. PI 20062710, May 9, 2009, 4 pages.
Neon Product Information Datasheets [online]. "Enterprise Casino Management, Table Management System, Mobile, Gaming". Intelligent Gaming, 2014. Retrieved on Oct. 12, 2016 from the Internet: <URL: http://www.intelligentgaming.co.uk/products/neon-enterprise/> (4 pages).
PCT International Preliminary Examination Report for International Patent Application No. PCT/US02/31105 dated Jul. 28, 2004, 9 pages.
PCT International Search Report for International Application No. PCT/US2003/015393, dated Oct. 6, 2003, 2 pages.
PCT International Search Report for PCT/US2005/034737 dated Apr. 7, 2006, 1 page (WO06/039308).
PCT International Search Report for PCT/US2007/022894, dated Jun. 11, 2008, 3 pages.
PCT International Search Report and Written Opinion, PCT/US2012/48706, dated Oct. 16, 2012, 12 pages.
PCT International Search Report and Written Opinion of the International Searching Authority for PCT/US2010/001032, dated Jun. 16, 2010, 11 pages.
PCT International Search Report and Written Opinion for PCT/US07/15035, dated Sep. 29, 2008, 6 pages.

(56) References Cited

OTHER PUBLICATIONS

PCT International Search Report and Written Opinion for PCT/US07/15036, dated Sep. 23, 2008, 6 pages.
PCT International Search Report and Written Opinion, PCT Application No. PCT/US2015/051038, dated Jan. 22, 2016, 11 pages.
PCT International Search Report and Written Opinion of the International Searching Authority for PCT/US2008/007069, dated Sep. 8, 2008, 10 pages.
PCT International Search Report and Written Opinion, PCT Application No. PCT/US2015/022158, dated Jun. 17, 2015, 13 pages.
PCT International Search Report and Written Opinion for International Application No. PCT/US2007/023168, dated Sep. 12, 2008, 8 pages.
PCT International Search Report and Written Opinion, PCT Application No. PCT/US2015/040196, dated Jan. 15, 2016, 20 pages.
PCT International Search Report and Written Opinion, PCT Application No. PCT/US2013/062391, dated Dec. 17, 2013, 13 pages.
PCT International Search Report and Written Opinion of the International Searching Authority for PCT/U505/31400, dated Sep. 25, 2007, 12 pages.
PCT International Search Report and Written Opinion, PCT Application No. PCT/US2015/025420, dated Oct. 2, 2015, 15 pages.
PCT International Search Report and Written Opinion of the International Searching Authority for PCT/US13/59665, dated Apr. 25, 2014, 21 pages.
PCT International Search Report and Written Opinion of the International Searching Authority for PCT/IB2013/001756, dated Jan. 10, 2014, 7 pages.
PCT International Search Report and Written Opinion of the International Searching Authority for PCT/US11/59797, dated Mar. 27, 2012, 14 pages.
PCT International Search Report and Written Opinion for International Application No. PCT/US2007/022858, dated Mar. 7, 2008, 7 pages.
PCT International Search Report and Written Opinion for International Patent Application No. PCT/US2006/22911, dated Jun. 1, 2007, 6 pages.
PCT International Search Report and Written Opinion of the International Searching Authority for PCT/GB2011/051978, dated Jan. 17, 2012, 11 pages.
Philippines Patent Application Formality Examination Report—Philippines Patent Application No. 1-2006-000302, dated Jun. 13, 2006.
"Playtech Retail begins roll out of Neon across Grosvenos 55 UK Casinos". Playtech, Apr. 21, 2016. Retrieved on Oct. 11, 2016 from the Internet: <URL: https://www.playtech.com/news/latest_news_and_prs/playtech_retail_begins_roll_out_of_neon_across_grosvenor_s_55_uk_casinos> (1 page).
Press Release for Alliance Gaming Corp., Jul. 26, 2004—Alliance Gaming Announces Control with Galaxy Macau for New MindPlay Baccarat Table Technology, 2 pages, http://biz.yahoo.com/prnews.
Scarne's Encyclopedia of Games by John Scarne, 1973, "Super Contract Bridge", p. 153.
Shuffle Master Gaming, Service Manual, ACETM Single Deck Card Shuffler, (1998), 63 pages.
Shuffle Master Gaming, Service Manual, Let It Ride Bonus® With Universal Keypad, 112 pages, © 2000 Shuffle Master, Inc.
Service Manual/User Manual for Single Deck Shufflers: BG1, BG2 and BG3 by Shuffle Master © 1997, 151 page.
Singapore Patent Application Examination Report—Singapore Patent Application No. SE 2008 01914 A, dated Jun. 18, 2008, 9 pages.
SHFL Entertainment, Inc. Docket No. 60, Opening Claim Construction Brief, filed in Nevada District Court Case No. 2:12-cv-01782 with exhibits, Aug. 8, 2013, p. 1-125.
Shuffle Master's Reply Memorandum in Support of Shuffle Master's Motion for Preliminary Injunction for *Shuffle Master, Inc.* vs. *VendingData Corporaion*, In the U.S. District Court, District of Nevada, No. CV-S-04-1373-JCM-LRL, Nov. 29, 2004.

Statement of Relevance of Cited References, Submitted as Part of a Third-Party Submission Under 37 CFR 1.290 on Dec. 7, 2012 (12 pages).
⅓" B/W CCD Camera Module EB100 by EverFocus Electronics Corp., Jul. 31, 2001, 3 pgs.
"ACE, Single Deck Shuffler," Shuffle Master, Inc., (2005), 2 pages.
Advansys, "Player Tracking" http://advansys.si/products/tablescanner/player-tracking/[Sep. 23, 2016 1:41:34 PM], 4 pages.
Australian Examination Report for Australian Application No. 2008202752, dated Sep. 25, 2009, 2 pages.
Australian Examination Report for Australian Application No. 2010202856, dated Aug. 11, 2011, 2 pages.
Australian Provisional Patent Application for Australian Patent Application No. PM7441, filed Aug. 15, 1994, Applicants: Rodney G. Johnson et al., Title: Card Handling Apparatus, 13 pages.
"Automatic casino card shuffle," Alibaba.com, (last visited Jul. 22, 2014), 2 pages.
Bally Systems Catalogue, Ballytech.com/systems, 2012, 13 pages.
Canadian Office Action for CA 2,580,309 dated Mar. 20, 2012 (6 pages).
Canadian Office Action for Canadian Application No. 2,461,726, dated Jul. 19, 2010, 3 pages.
Canadian Office Action for Canadian Application No. 2,461,726, dated Dec. 11, 2013, 3 pages.
CasinoTrac TableTrac Services. Product Information Datasheet [online]. CasinoTrac, 2015. Retrieved on Oct. 12, 2016 from the Internet: <URL: http://www.tabletrac.com/?pageid=15#prettyPhoto> (3 pages).
Christos Stergiou and Dimitrios Siganos, "Neural Networks," http://www.doc.ic.ac.uk/~nd/surprise_96/journal/vol4/cs11/report.html (13 pages), Dec. 15, 2011.
Complaint filed in the matter of *SHFL entertainment, In.* v. *DigiDeal Corporation*, U.S. District Court, District of Nevada, Civil Action No. CV 2:12-cv-01782-GMC-VCF, Oct. 10, 2012, 62 pages.
Connect2Table Administrator Manual, Jan. 7, 2013 (82 pages).
Connect2Table Quick Installation Guide, Feb. 20, 2013 (36 pages).
Connect2Table Connect2Table System Summary, generated Oct. 21, 2016 (2 pages).
Connect2Table User Manual. Feb. 7, 2013 (35 pages).
Documents submitted in case of *Shuffle Master, Inc.* v. *Card Aurstia, et al.*, Case No. CV-N-0508-HDM-(VPC) Consolidated with Case No. CV-N-02-0244-ERC-(RAM)), May 6, 2003, scan of color pages, for clarity, Part 18 of 23 (color copies from Binder 1).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 1 of 23 (Master Index and Binder 1, 1 of 2).
Documents submitted in the case of *Shuffle Master, Inc.* v. *Card Austria, et al,* Case No. CV-N-0508-HDM-(VPC) (Consolidated with Case No. Cv-N-02-0244-ERC-(RAM)), May 6, 2003, Part 2 of 23 (Master Index and Binder 1, 2 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 3 of 23 (Binder 2, 1 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 4 of 23 (Binder 2, 2 of 2).
Documents submitted in case of *Shuffle Master, Inc.* v. *Card Aurstia, et al.*, Case No. CV-N-0508-HDM-(VPC) Consolidated with Case No. CV-N-02-0244-ERC-(RAM)), May 6, 2003, scan of color pages, for clarity, Part 19 of 23 (color copies from Binder 3).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 5 of 23 (Binder 3, 1 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 6 of 23 (Binder 3, 2 of 2).

(56) References Cited

OTHER PUBLICATIONS

Documents submitted in case of *Shuffle Master, Inc.* v. *Card Aurstia, et al.*, Case No. CV-N-0508-HDM-(VPC) Consolidated with Case No. CV-N-02-0244-ERC-(RAM)), May 6, 2003, scan of color pages, for clarity, Part 20 of 23 (color copies from Binder 4).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 7 of 23 (Binder 4, 1 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 8 of 23 (Binder 4, 2 of 2).
Documents submitted in case of *Shuffle Master, Inc.* v. *Card Aurstia, et al.*, Case No. CV-N-0508-HDM-(VPC) Consolidated with Case No. CV-N-02-0244-ERC-(RAM)), May 6, 2003, scan of color pages, for clarity, Part 21 of 23 (color copies from Binder 6).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 10 of 23 (Binder 6, 2 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 9 of 23 (Binder 5 having no contents; Binder 6, 1 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 11 of 23 (Binder 7, 1 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 12 of 23 (Binder 7, 2 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 13 of 23 (Binder 8, 1 of 5).
Documents submitted in case of *Shuffle Master, Inc.* v. *Card Aurstia, et al.*, Case No. CV-N-0508-HDM-(VPC) Consolidated with Case No. CV-N-02-0244-ERC-(RAM)), May 6, 2003, scan of color pages, for clarity, Part 22 of 23 (color copies from Binder 8, part 1 of 2).
Documents submitted in case of *Shuffle Master, Inc.* v. *Card Aurstia, et al.*, Case No. CV-N-0508-HDM-(VPC) Consolidated with Case No. CV-N-02-0244-ERC-(RAM)), May 6, 2003, scan of color pages, for clarity, Part 23 of 23 (color copies from Binder 8, part 2 of 2).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 14 of 23 (Binder 8, 2 of 5).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 15 of 23 (Binder 8, 3 of 5).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 16 of 23 (Binder 8, 4 of 5).
Documents submitted in the case of *Shuffle Master, Inc.* v. *Card Austria, et al.*, Case No. CV-N-0508-HDM-(VPC) (Consolidated with Case No. CV-N-02-0244-ERC-(RAM)), May 6, 2003, Part 17 of 23 (Binder 8, 5 of 5).
DVD labeled Exhibit 1. This is a DVD taken by Shuffle Master personnel of the live operation of a CARD One2Sil Shuffler (Oct. 7, 2003). DVD sent to Examiner by US Postal Service with this PTO/SB/08 form.
"Error Back propagation," http://willamette.edu~gorr/classes/cs449/backprop.html (4 pages), Nov. 13, 2008.
"i-Deal," Bally Technologies, Inc., (2014), 2 pages.
"Shufflers—SHFL entertainment," Gaming Concepts Group, (2012), 6 pages.
"TAG Archives: Shuffle Machine," Gee Wiz Online, (Mar. 25, 2013), 4 pages.
"TableScanner (TM) from Advansys", Casino Inside Magazine, No. 30, pp. 34-36 (Dec. 2012) (4 pages).
TableScanner "Accounting & Cage". Product Information Datasheets [online]. Advansys, 2013. Retrieved on Oct. 11, 2016 from the Internet: <URL: http://advansys.si/products/tablescanner/accounting-cage/> (4 pages).
TableScanner "Casino Management System". Product Information Datasheets [online]. Advansys, 2013. Retrieved on Oct. 11, 2016 from the Internet: <URL: http://advansys.si/> (6 pages).
TableScanner "Multisite". Product Information Datasheets [online]. Advansys, 2013. Retrieved on Oct. 11, 2016 from the Internet: <URL: http://advansys.si/products/tablescanner/multisite/> (3 pages).
TableScanner "Player Tracking". Product Information Datasheets [online]. Advansys, 2013. Retrieved on Sep. 23, 2016 from the Internet: <URL: http://advansys.si/products/tablescanner/player-tracking/> (4 pages).
TableScanner "Table Management system". Product Information Datasheets [online]. Advansys, 2013. Retrieved on Oct. 11, 2016 from the Internet: <URL: http://advansys.si/products/tablescanner/> (4 pages).
tbm=pts&hl=en Google Search for card handling device with storage area, card removing system pivoting arm and processor; http://www.google.com/?tbrn=pts&hl=en; Jul. 28, 2012, 2 pages.
Tracking the Tables, by Jack Bularsky, Casino Journal, May 2004, vol. 17, No. 5, pp. 44-47.
"TYM @ A Glance—Table Games Yield Management", TYM Live Product Information Datasheets [online]. TANGAM Systems, 2016. Retrieved on Oct. 3, 2016 from the Internet: <URL: http://tangamgaming.com/wp-content/uploads/2016/12/TG_TYMGlance_2016-V4-1.pdf> (2 pages).
United States Court of Appeals for the Federal Circuit Decision Decided Dec. 27, 2005 for Preliminary Injuction for *Shuffle Master, Inc.* vs. *VendingData Corporation*, In the U.S. District Court, District of Nevada, No. CV-S-04-1373-JCM-LRL.
VendingData Corporation's Answer and Counterclaim Jury Trial Demanded for *Shuffle Master, Inc.* vs. *VendingData Corporation*, In the U.S. District Court, District of Nevada, No. CV-S-04-1373-JCM-LRL, Oct. 25, 2004.
VendingData Corporation's Opposition to Shuffle Master Inc.'s Motion for Preliminary Injection for *Shuffle Master, Inc.* vs. *VendingData Corporation*, In the U.S. District Court, District of Nevada, No. CV-S-04-1373-JCM-LRL, Nov. 12, 2004.
VendingData Corporation's Responses to Shuffle Master, Inc.'s First set of interrogatories for *Shuffler Master, Inc.* vs. *VendingData Corporation*, In the U.S. District Court, District of Nevada, No. CV-S-04-1373-JCM-LRL, Mar. 14, 2005.
Shuifie Master, Inc. (1996). Let It Ride, The Tournament, User Guide, 72 pages.

\* cited by examiner

APPARATUS, SYSTEM, METHOD, AND COMPUTER-READABLE MEDIUM FOR CASINO CARD HANDLING WITH MULTIPLE HAND RECALL FEATURE

CROSS-REFERENCE TO RELATED APPLICATIONS

This application is a continuation of U.S. patent application Ser. No. 15/043,241, filed Feb. 12, 2016, now U.S. Pat. No. 9,633,523, issued Apr. 25, 2017, which is a continuation of U.S. patent application Ser. No. 14/330,964, filed Jul. 14, 2014, now U.S. Pat. No. 9,259,640, issued Feb. 16, 2016, which, in turn, is a continuation of U.S. patent application Ser. No. 13/311,166, filed Dec. 5, 2011, now U.S. Pat. No. 8,777,710, issued Jul. 15, 2014, which, in turn, is a continuation of U.S. patent application Ser. No. 11/810,864, filed Jun. 6, 2007, now U.S. Pat. No. 8,070,574, issued Dec. 6, 2011. The present application is also related to U.S. patent application Ser. No. 11/598,259, titled "CARD HANDLING DEVICES AND METHODS OF USING THE SAME," now U.S. Pat. No. 7,766,332, issued Aug. 3, 2010, and U.S. patent application Ser. No. 11/481,407, titled "CARD SHUFFLER WITH ADJACENT CARD INFEED AND CARD OUTPUT COMPARTMENTS," now U.S. Pat. No. 8,342,525, issued Jan. 1, 2013, the disclosure of each of which is hereby incorporated by reference in its entirety herein. This application is also related to U.S. patent application Ser. No. 12/848,631, filed Aug. 2, 2010, now U.S. Pat. No. 8,141,875, issued Mar. 27, 2012, U.S. patent application Ser. No. 13/422,167, filed Mar. 16, 2012, now U.S. Pat. No. 8,931,779, issued Jan. 13, 2015, and U.S. patent application Ser. No. 13/431,757, filed Mar. 27, 2012. This application is also related to U.S. patent application Ser. No. 13/714,211, filed Dec. 13, 2012, now U.S. Pat. No. 8,702,101, issued Apr. 22, 2014.

FIELD

Embodiments of the present disclosure relate generally to the field of gaming and the field of casino table card gaming. More particularly, embodiments of the disclosure relate to the use of equipment for the delivery of playing cards.

BACKGROUND

Wagering games based on the outcome of randomly generated arrangements of cards are well known. Such games are widely played in gaming establishments and, often, a single deck of 52 playing cards is used to play the game. Some games use multiple decks of cards (typically six or eight decks), such as blackjack and baccarat. Other games use two decks of cards, such as double deck blackjack. Many specialty games use single decks of cards, with or without jokers and with or without selected cards removed. Examples of such games include THREE CARD POKER®, LET IT RIDE®, CARIBBEAN STUD POKER®, SPANISH 21®, FOUR CARD POKER®, CRAZY 4 POKER® and others. As new games are developed, card shufflers are modified to be used in connection with the new games.

From the perspective of players, the time the dealer must spend in shuffling diminishes the excitement of the game. From the perspective of casinos, shuffling time reduces the number of hands played and specifically reduces the number of wagers placed and resolved in a given amount of time, consequently reducing casino revenue. Casinos would like to increase the amount of revenue generated by a game without changing the game or adding more tables. One approach is to simply speed up play. One option to increase the speed of play is to decrease the time the dealer spends shuffling.

The desire to decrease shuffling time has led to the development of mechanical and electromechanical card shuffling devices. Such devices increase the speed of shuffling and dealing, thereby increasing actual playing time. Such devices also add to the excitement of a game by reducing the amount of time the dealer or house has to spend in preparing to play the game.

Dealers appreciate using card shufflers that place the minimum strain on the dealer's hands, back and arms. Some existing shuffler designs put unnecessary strain on the muscles of the users. Dealers prefer shufflers that are low profile, especially when the shuffler dispenses cards into a game rather than shuffle batches of cards for shoe games.

Numerous approaches have been taken to the design of card shufflers. These approaches include random ejection designs (e.g., U.S. Pat. Nos. 6,959,925; 6,698,756; 6,299,167; 6,019,368; 5,676,372; and 5,584,483), stack separation and insertion (e.g., U.S. Pat. Nos. 5,683,085 and 5,944,310), interleaving designs (e.g., U.S. Pat. Nos. 5,275,411 and 5,695,189), for example, random insertion using a blade (U.S. Pat. No. 5,382,024) and designs that utilize multiple shuffling compartments.

One such example of a compartment shuffler is disclosed in U.S. Pat. No. 4,586,712 to Lorber et al. The automatic shuffling apparatus disclosed is designed to intermix multiple decks of cards under the programmed control of a computer. The apparatus is a carousel-type shuffler having a container, a storage device for storing shuffled playing cards, a removing device and an inserting device for intermixing the playing cards in the container, a dealing shoe and supplying means for supplying the shuffled playing cards from the storage device to the dealing shoe. The container includes multiple card-receiving compartments, each one capable of receiving a single card.

Another shuffler having mixing compartments arranged in a carousel is disclosed in U.S. Pat. No. 6,267,248 to Johnson et al. Cards are loaded into an infeed tray, fed sequentially past a card-reading sensor and are inserted into compartments within a carousel to either randomize or sort cards into a preselected order. The carousel moves in two directions during shuffling. U.S. Pat. No. 6,676,127 to Johnson et al. describes another variation of the shuffler, in which cards are inserted into and removed from a same side of the carousel, with the card infeed tray being located above the discard tray (see FIG. 3).

U.S. Pat. No. 3,897,954 to Erickson et al. discloses a device for delivering cards, one at a time, into one of a number vertically stacked card-shuffling compartments. A logic circuit is used to determine the sequence for determining the delivery location of a card. The card shuffler can be used to deal stacks of shuffled cards to a player.

U.S. Pat. No. 4,770,421 to Hoffman discloses a card-shuffling device including a card loading station with a conveyor belt. The belt moves the lowermost card in a stack onto a distribution elevator whereby a stack of cards is accumulated on the distribution elevator. Adjacent to the elevator is a vertical stack of mixing pockets. A microprocessor preprogrammed with a finite number of distribution schedules sends a sequence of signals to the elevator corresponding to heights called out in the schedule. Single cards are moved into the respective pocket at that height. The distribution schedule is either randomly selected or schedules are executed in sequence. When the microprocessor completes the execution of a single distribution cycle, the cards are removed a stack at a time and loaded into a second elevator. The second elevator delivers cards to an output reservoir.

U.S. Pat. No. 5,275,411 to Breeding discloses a machine for automatically shuffling and dealing hands of cards. Although this device does not shuffle cards by distributing cards to multiple compartments, the machine is the first of its kind to deliver randomly arranged hands of cards to a casino card game. A single deck of cards is shuffled and then cards are automatically dispensed into a hand-forming tray. The shuffler includes a deck-receiving zone, a carriage section for separating a deck into two deck portions, a sloped mechanism positioned between adjacent corners of the deck portions, and an apparatus for snapping the cards over the sloped mechanism to interleave the cards. The Breeding shuffler was originally designed to be used in connection with single deck poker style games such as LET IT RIDE® stud poker and a variant of pai gow poker marketed as WHO'S FIRST® Pai Gow Poker.

In an attempt to speed the rate of play of specialty table games equipped with a shuffler, the ACE® card shuffler as disclosed in U.S. Pat. Nos. 6,149,154, 6,588,750, 6,655,684 and 7,059,602 was developed. This shuffler operates at faster speeds than previously known shuffler devices described above, has fewer moving parts, and requires much shorter set up time than the prior designs. The shuffler includes a card infeed tray, a vertical stack of shuffling compartments and a card output tray. A first card moving mechanism advances cards individually from the infeed tray into a compartment. A processor randomly directs the placement of fed cards into the compartments, and an alignment of each compartment with the first card mover, forming random groups of cards within each compartment. Groups of cards are unloaded by a second card-moving mechanism into the output tray.

Another compartment shuffler capable of delivering randomly arranged hands of cards for use in casino card games is the ONE-2-SIX® shuffler (developed by Casino Austria Research & Development (CARD)). This shuffler is disclosed in U.S. Pat. Nos. 6,659,460 and 6,889,979. This shuffler is capable of delivering randomly arranged hands of cards when a first delivery end is attached, and is capable of delivering a continuous supply of cards from a shoe-type structure when a second delivery end is attached. Cards are fed from a feeder individually into compartments within a carousel to accomplish random ordering of cards.

Most of the shuffler designs mentioned above are high profile and require loading cards into the rear of the machine, and then removing cards from the front of the machine. The cards must be lifted over the top of the machine to return spent cards to the infeed tray, causing a dealer to lift his arm over the top of the machine at the conclusion of each round of play. Newer shuffler designs are flush-mounted into a gaming table surface. One such shuffler of this type is disclosed in U.S. Pat. No. 6,651,982.

One particular type of card shuffling device is referred to as a batch type shuffler. One characteristic of a (single or double deck) batch type shuffler is that when all of the cards are dispensed in a round of play, the remaining cards in the pack (one or two decks) are removed and then reinserted. In use, while the game is being dealt using a first deck, a second deck of cards is being randomized and arranged into groups. A discard rack is typically provided on the table so that cards removed from the game are staged in the rack while the other deck of cards is being processed. Following this procedure avoids the possibility that cards will be returned to the input tray and that the two decks will be intermingled. The use of two separate decks (one at a time) speeds game play because shuffling of a first deck occurs during play with a second deck.

Continuous shufflers, in contrast, are not unloaded at the end of a round of play. Spent cards are returned and inserted, and new cards dispensed without removing the entire set.

U.S. Pat. No. 6,959,925 to Sines discloses a single deck continuous card shuffler known in the trade as the POKER-ONE®. This shuffler avoids the alternating use of two different decks of cards during a specialty card game by providing a continuous supply of cards to a card game. Although this shuffler uses only one deck of cards, the shuffler does not verify that the correct number of cards (typically 52) are present prior to each shuffle, and consequently player cheating by inserting extra cards would go undetected.

Shufflers that communicate with network-based game systems have been described in the art. An example is described in U.S. Patent Publication No. 2003/0064798A1. A shuffler with an on board microprocessor and communication port communicates with a local processor and/or a central processor. The local or central processor may manage a game system.

Using these card-handling devices, there are still many variables that can affect a Casino's margin of profit, one of which is the accuracy of a dealer in settling bets during any game play. Each table game in a casino is designed with a certain house advantage. The payouts for any winning hand are pre-determined by the game developer based on rigorous math analysis. Although it is a requirement that a dealer must be able to recognize all winning hands (of all different card combinations) and pay out appropriate amounts, it is common that a dealer makes mistakes by either misreading a hand or paying the wrong amount to a player with a winning hand.

Therefore, there is a need for a shuffler that has all of the performance attributes of known shufflers and enables checking the accuracy of casino games by detecting, storing, and retrieving information about the composition of present and past hands of cards in a casino table game.

BRIEF SUMMARY

The present invention, in various embodiments, comprises methods, devices, systems, and computer-readable media configured for detecting, storing, and retrieving information about the composition of present and past hands of cards dispensed in a casino table game.

An embodiment of the invention includes an apparatus that includes a card-handling device, a card recognition system, a control system, and a display. The card-handling device may be used for randomizing and dispensing cards during a casino table game play. The cards may be dispensed as a plurality of hands, each hand including one or more cards. The card recognition system identifies card information including a rank and a suit of each card while each card is under the control of the card-handling device. The control system includes one or more processors and a memory. The control system is configured to control the card-handling device and receive the card information for each card from the card recognition system. The control system is also configured to maintain a play history including a card composition of a plurality of rounds. The card composition includes card information for each hand of each round. Finally, the card information of at least one hand from at least one round of play is presented on the display.

Another embodiment of the invention comprises a system that includes: (1) a card-handling device, (2) an object recognition device, and (3) a table manager. The card-handling device may be used for randomizing and dispensing cards during a casino table game play wherein the cards may be dispensed as a plurality of hands, each hand including one or more cards. The card-handling device includes a card recognition system for recognizing card information including a rank and a suit of each card while each card is under control of the card-handling device. The system also includes one or more processors for receiving the card information for each card from the card recognition system and determining the cards in each hand of a current round. The object recognition device identifies at least one betting object indicating at least one active player position for the current round. The table manager includes a computer and a display and is configured to receive position information about the at least one active player position from the object recognition device. The table manager also receives the card information from within the card-handling device and analyzes the card information and the position information to display the card information for the at least one active player position. In other embodiments, card information is determined in a processor external to the card-handling device.

Yet another embodiment of the invention includes a method of providing cards during casino table game play. The method includes causing a card-handling device to substantially automatically generate a plurality of hands wherein each hand includes one or more cards. The method also includes identifying card information including a rank and a suit of each card as the card moves through the card-handling device. The method further includes maintaining a play history including a card composition for a plurality of rounds wherein the card composition of each round includes the cards in each hand of the round. Finally, the method includes displaying the card information of at least one hand from at least one round. The display may be mounted to the card-handling device or may be a separate system component.

Yet another embodiment of the invention includes a computer-readable medium including computer-executable instructions which, when executed on one or more computers, perform the method recited above.

DETAILED DESCRIPTION

Figure 1:
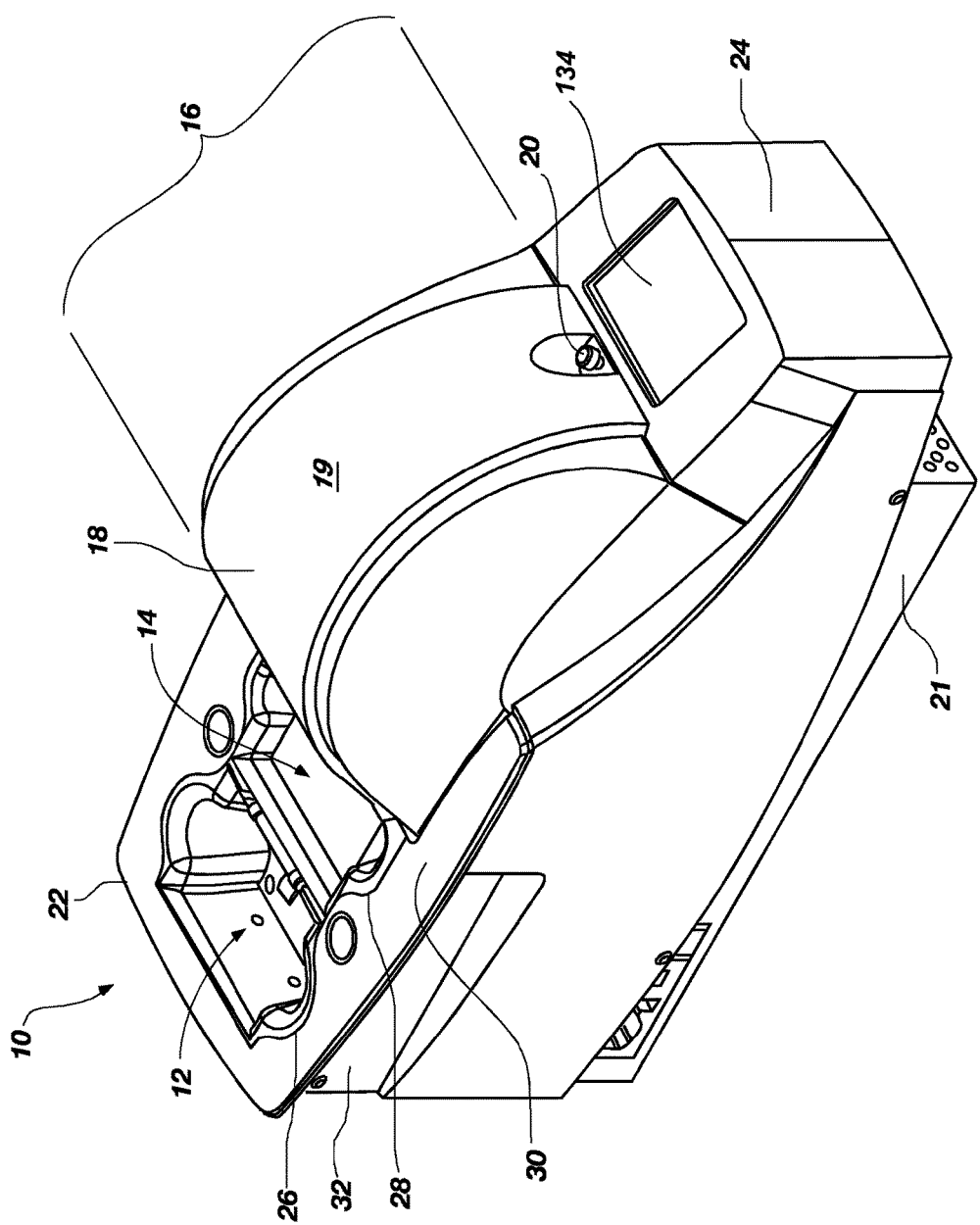
FIG. 1 is a perspective view of an embodiment of a card-handling device.

The present invention, in various embodiments, comprises methods, devices, and systems configured for detecting, storing, and retrieving information about the composition of present and past hands of cards in a casino table game.

The following provides a more detailed description of embodiments of the present invention. In this description, circuits and functions may be shown in block diagram form in order not to obscure the present invention in unnecessary detail. Conversely, specific implementations shown and described are exemplary only and should not be construed as the only way to implement the present invention unless specified otherwise herein. Additionally, block definitions and partitioning of functions between various blocks is exemplary of a specific implementation. It will be readily apparent to one of ordinary skill in the art that the present invention may be practiced by numerous other partitioning solutions.

Further, the term "module" is used herein in a non-limiting sense and solely to indicate functionality of particular circuits and assemblies included within embodiments of the invention, and may not be construed as requiring a particular physical structure, or particular partitioning between elements of the invention performing indicated functions.

In this description, some drawings may illustrate signals as a single signal for clarity of presentation and description. Persons of ordinary skill in the art will understand that the signal may represent a bus of signals, wherein the bus may have a variety of bit widths and the present invention may be implemented on any number of data signals including a single data signal.

Software processes illustrated herein are intended to illustrate representative processes that may be performed by the systems illustrated herein. Unless specified otherwise, the order in which the process acts are described is not intended to be construed as a limitation, and acts described as occurring sequentially may occur in a reverse sequence, or in one or more parallel process streams. Furthermore, the processes may be implemented in any suitable hardware, software, firmware, or combinations thereof.

When executed as firmware or software, the instructions for performing the processes may be stored on a computer-readable medium. A computer-readable medium includes, but is not limited to, magnetic and optical storage devices such as disk drives, magnetic tape, CDs (compact disks), DVDs (digital versatile discs or digital video discs), and semiconductor devices such as RAM, DRAM, ROM, EPROM, and Flash memory.

The disclosures of all patents, published patent applications, and other documents cited in this entire application are incorporated by reference in their respective entireties herein, whether or not such incorporation is specifically asserted in association with such citation.

Card-handling devices that embody teachings of the present invention may include major components that are physically arranged (for example, in a linear arrangement) in the following order: a) a playing card input compartment; b) a playing card retrieval compartment; and c) a playing card-handling zone. Playing cards may be moved from the playing card input compartment into the playing card-handling zone and from the playing card-handling zone into the playing card retrieval compartment. Furthermore, card-handling devices that embody teachings of the present invention may be configured to enable a user to either shuffle or selectively sort cards into a predefined order using the card-handling devices.

A perspective view of a card-handling device 10 according to embodiments of the present invention is shown in FIG. 1. The card-handling device 10 includes a card infeed tray 12, a card output tray 14, and a card-handling system or mechanism, which is described in further detail below. In some embodiments, the card output tray 14 may be removable for maintenance.

In some embodiments, the card infeed tray 12 and the card output tray 14 may be disposed adjacent one another. Furthermore, the card infeed tray 12 and the card output tray 14 each may be located near a first end 22 of the card-handling device 10. In some embodiments, the card infeed tray 12 and the card output tray 14 may each include a recessed area in the card-handling device 10, as shown in FIG. 1.

A major portion of the card-handling system may be located within a card-handling zone 16 of the card-handling device 10. The card-handling system may be enclosed within a cover 18, which, in this embodiment, has a curved upper surface 19 that is arched to enclose an upper portion of a carousel member (which is part of the card-handling system described in further detail below). The cover 18 may include a lock 20 to secure the cover 18 to a frame (not shown) of the card-handling device 10 to prevent unauthorized access to cards in the card-handling device 10. This locking feature advantageously allows a casino operator to shut down a table with cards loaded into the card-handling device 10. When the table is reopened, the operator can be assured that the cards held in the machine are secure. The key to the lock may be held by pit management, and the fact that the cover is, and has been, locked may eliminate any need to unload and verify the rank and suit of each card before play is resumed. Securing the cards within the card-handling device 10 when the machine is not in use is a valuable time and labor saving feature. The lock 20 may be located proximate a second end 24 of the card-handling device 10. Although an exemplary lock is a simple mechanical lock with rollers and a key, other locking systems may be used, such as, for example, electronic locks with keypad controls, locking systems that receive radio frequency identification (RFID) signatures, and computer-controlled locks.

Figure 2:
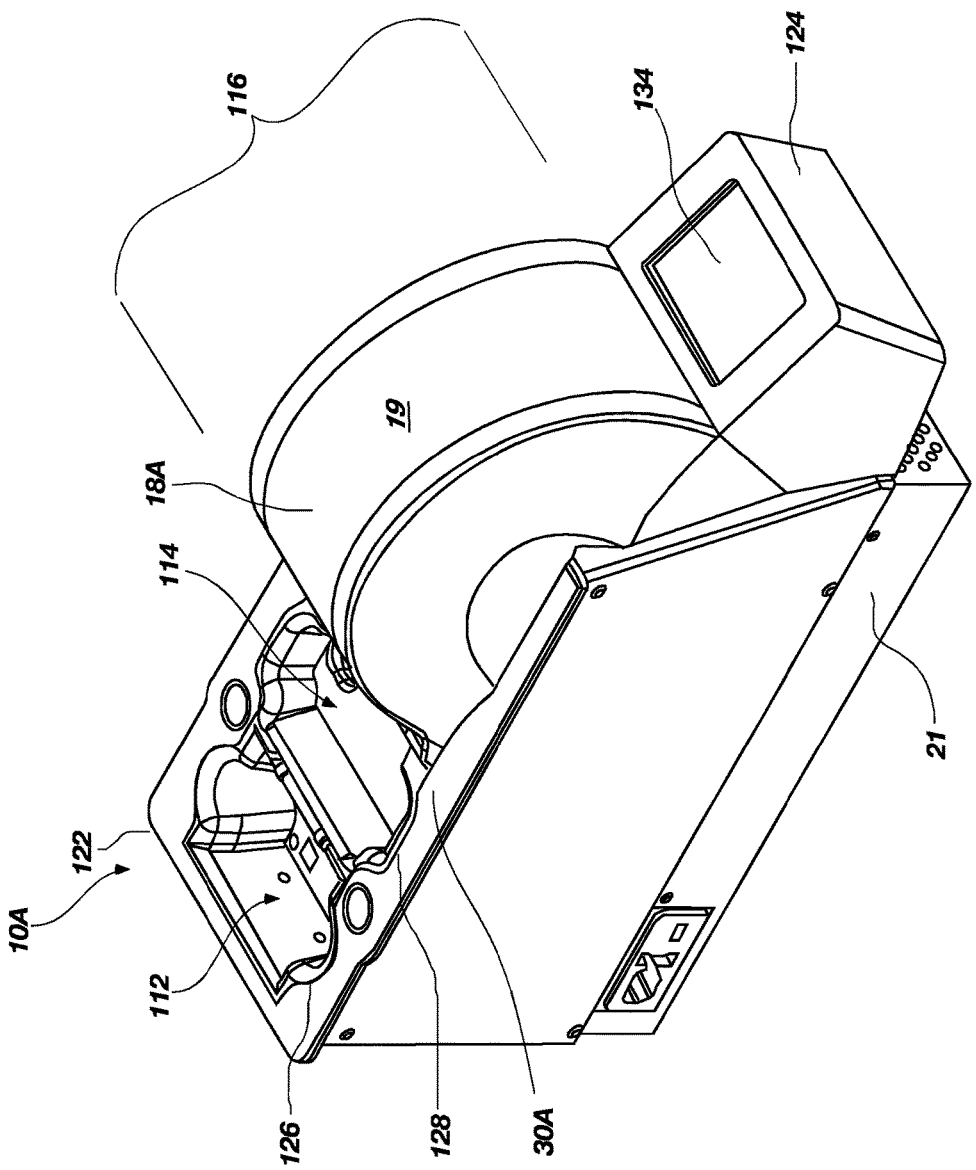
FIG. 2 is a perspective view of another embodiment of a card-handling device.

Additional card-handling devices according to embodiments of the present invention may not include an outer cover that is intended to be opened or removed by a user. For example, FIG. 2 illustrates another card-handling device 10A according to embodiments of the present invention that includes an outer cover 18A that is not intended to be opened or removed by a user. The card-handling device 10A may be otherwise substantially similar to the card-handling device 10, and may include a card infeed compartment 112, a card delivery compartment 114 near a first end 122 of the card-handling device 10A, and a card-handling zone 116 and a display 134 near a second end 124 of the card-handling device 10A. A card-handling mechanism comprising a carousel (not shown) is enclosed within the outer cover 18A. The outer cover 18A may be secured to the frame 21 and may be removable for maintenance, but may not be configured for removal by a user. In some embodiments, the outer cover 18A may be secured to the frame 21 with sheet metal screws. The card-handling device 10A may further include a flange 30A that intersects an upper edge 126 of the card infeed compartment 112 and an upper edge 128 of the card delivery compartment 114 and extends a portion of the way through the card-handling zone 116. This flange 30A may be mounted on a gaming table surface such that a portion of the card-handling zone 116 is positioned within the outside perimeter of the gaming table. A display 134 may be positioned at an elevation below the gaming table surface when the card-handling device 10A is mounted on or in a gaming table. The card-handling device 10A may be supported by the flange 30A, a table extension (not shown), a pedestal, a combination of the above, or by any other support technique.

Referring back to FIG. 1, the card infeed tray 12 and the card output tray 14 may be surrounded by a substantially flat flange 30 that intersects the upper edge 26 of the card infeed tray 12 and the upper edge 28 of the card output tray 14. In this configuration, the flat flange 30, the upper edge 26 of the card infeed tray 12, and the upper edge 28 of the card output tray 14 may be disposed in substantially the same plane. In other words, the upper edge 26 of the card infeed tray 12 and the upper edge 28 of the card output tray 14 may be substantially co-planar. In such a configuration, the card-handling device 10 may be mounted for use on or in a gaming table such that the flat flange 30, the upper edge 26 of the card infeed tray 12, and the upper edge 28 of the card output tray 14 are substantially flush with the upper surface of the gaming table.

In one mounting arrangement, a gaming table surface may be provided with a notch cut into an edge of the table facing the dealer. The first end 22 of the card-handling device 10 may include a recess 32 that has a size and shape that is configured to receive the side of the table therein along the notch. The remainder of the card-handling device 10 (e.g., the second end 24 of the card-handling device 10) may be supported by a support bracket beneath the table surface. In this configuration, the portion of the card-handling device 10 that is inserted into the gaming table may be flush mounted with the upper surface of the table.

In the arrangement described above, the first end 22 of the card-handling device 10 may be nearest the players and the second end 24 of the card-handling device 10 may be nearest the pit when the card-handling device 10 is mounted on or in a gaming table. Furthermore, the card-handling zone 16 may be located behind or to the side of the dealer and out of the way when the card-handling device 10 is mounted on or in the gaming table.

Because the card infeed tray 12 and the card output tray 14 are located on the same side of the card-handling zone 16 (near the first end 22 of the card-handling device 10), the cards may be more accessible to the dealer, and the dealer need not lift cards over the card-handling zone 16 to place spent cards back into the card-handling zone 16. The present design, therefore, may be relatively more ergonomically beneficial to the user (dealer) than known designs. Positioning the card infeed tray 12 at the table level also may reduce the possibility that card faces will be accidentally shown to players.

The placement of an upper edge 26 of the card infeed tray 12 and an upper edge 28 of the output tray 14 substantially in the same plane lying on, or proximate to, the gaming surface also may provide distinct ergonometric advantages. If the dealer moves his or her hands smaller distances during card handling, he or she is likely to experience fewer repetitive stress or strain injuries. Therefore, delivering spent cards to the card-handling device 10 at the gaming surface and retrieving freshly handled cards from substantially the same location or nearby offers distinct user advantages.

The placement of the infeed tray 12 and the output tray 14 on the same side of a carousel-type playing card-handling zone (discussed in further detail below) also allows the user to place spent cards-face down in the infeed tray 12, and at the same time receive fresh cards from the output tray 14 in a face-down configuration. This attribute has been previously described in U.S. Pat. No. 6,676,127 to Johnson et al. This feature improves the security of a carousel card-handling device 10, since no cards are exposed during loading, shuffling, or unloading.

A horizontally disposed centerline intersecting the card infeed tray 12 and the card output tray 14 may also advantageously intersect a centerline of the card-handling zone 16, as will be discussed in more detail below. This arrangement allows the machine to be fairly narrow in width and permits both card tray areas (but not the more bulky card-handling zone 16) to be located on or near the playing table surface.

The card-handling zone 16 of the card-handling device 10 may include card-moving elements located below the card infeed and output trays. The card-handling zone 16 may be capable of performing at least one of the following functions: a) shuffling, b) arranging cards into a desired order, c) verifying completeness of a group of cards, d) reading special markings on cards (such as, for example, a casino identification mark, a manufacturer identification mark, a special bonus card identification mark, a deck identification mark, etc.), e) scanning cards for unauthorized markings, f) identifying cards lacking required markings, g) measuring card wear, h) decommissioning cards, i) applying markings to cards, j) scanning cards for unauthorized electronic devices, k) delivering special cards such as, for example, bonus cards, promotional cards, or wild cards, and many other useful functions.

In some embodiments of the present invention, the card-handling zone 16 may comprise a card-handling system or mechanism comprising a temporary card storage device or system 244 (FIG. 8), a card infeed mechanism or system 240 (FIG. 8) for moving cards from the card infeed tray 12 to the temporary card storage system 244 (FIG. 8), and a card output mechanism or system 242 (FIG. 8) for moving cards from the temporary card storage system 244 (FIG. 8) to the card output tray 14. In some embodiments of the present invention, the temporary card storage system 244 (FIG. 8) may comprise a carousel device having multiple compartments for receiving cards therein, as discussed in further detail below. Many types of card-handling systems or mechanisms that include other types of temporary card storage devices may be utilized in card-handling devices that embody teachings of the present invention. Some non-limiting examples of such other types of card-handling systems or mechanisms include the card-handling system described in detail in U.S. Pat. No. 6,959,925 to Baker et al., the vertical compartment card-handling system described in U.S. Pat. No. 6,149,154 to Grauzer et al., and the card-handling system described in U.S. Pat. No. 6,651,981 to Grauzer et al.

Figure 3:
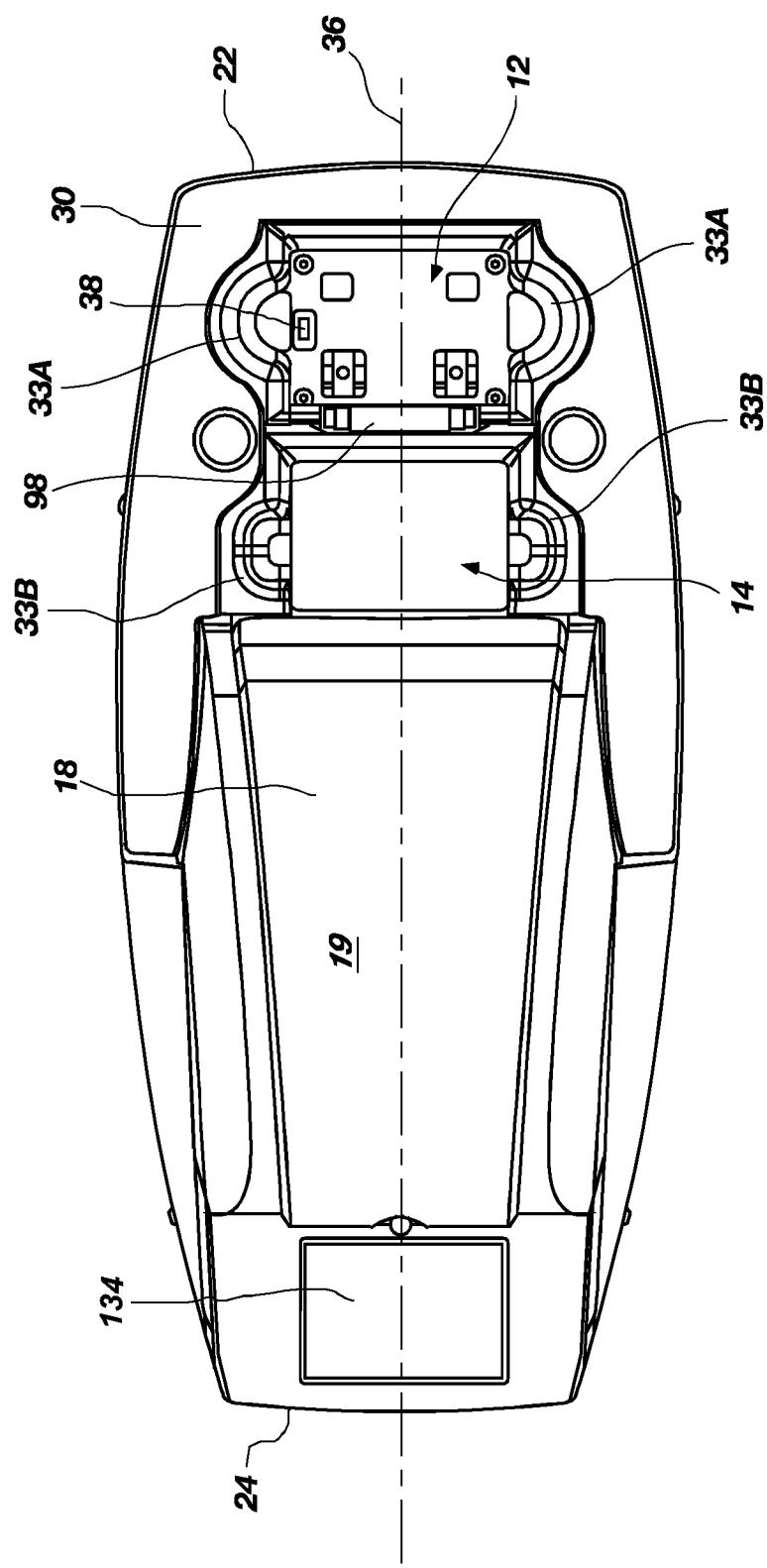
FIG. 3 is a top plan view of the card-handling device shown in FIG. 1.

FIG. 3 is a top plan view of the card-handling device 10 shown in FIG. 1. The card infeed tray 12 and the card output tray 14 may be positioned on the same side of the card-handling device 10 and in substantially a common plane. For example, the card infeed tray 12 and the card output tray 14 each may be positioned proximate the first end 22 of the card-handling device 10. Furthermore, the card infeed tray 12 and the card output tray 14 each may be positioned on the same side of the card-handling zone 16 (which may include, for example, a carousel 120, as discussed in further detail below). In some embodiments of the present invention, the card infeed tray 12 and the card output tray 14 each may be bisected by a centrally located longitudinal axis 36. Furthermore, in some embodiments, the card infeed tray 12 and the card output tray 14 each may be substantially symmetrically bisected by the longitudinal axis 36. As also shown in FIG. 3, the card infeed tray 12 may be equipped with a gate member 98 whose functions will be described in more detail below. The card infeed tray 12 also may include a sensor 38 configured to detect the presence of any card provided in the card infeed tray 12.

Declining finger cut-outs 33A or recesses may be provided in the interior surfaces of the card infeed tray 12, and declining finger cut-outs 33B or recesses may be provided in the interior surfaces of the card output tray 14. The finger cut-outs 33A and 33B may have a size and shape configured to receive or accommodate at least one digit of the hand of a person therein to facilitate handling of cards in the card infeed tray 12 and the card output tray 14 by a user.

Figure 4A:
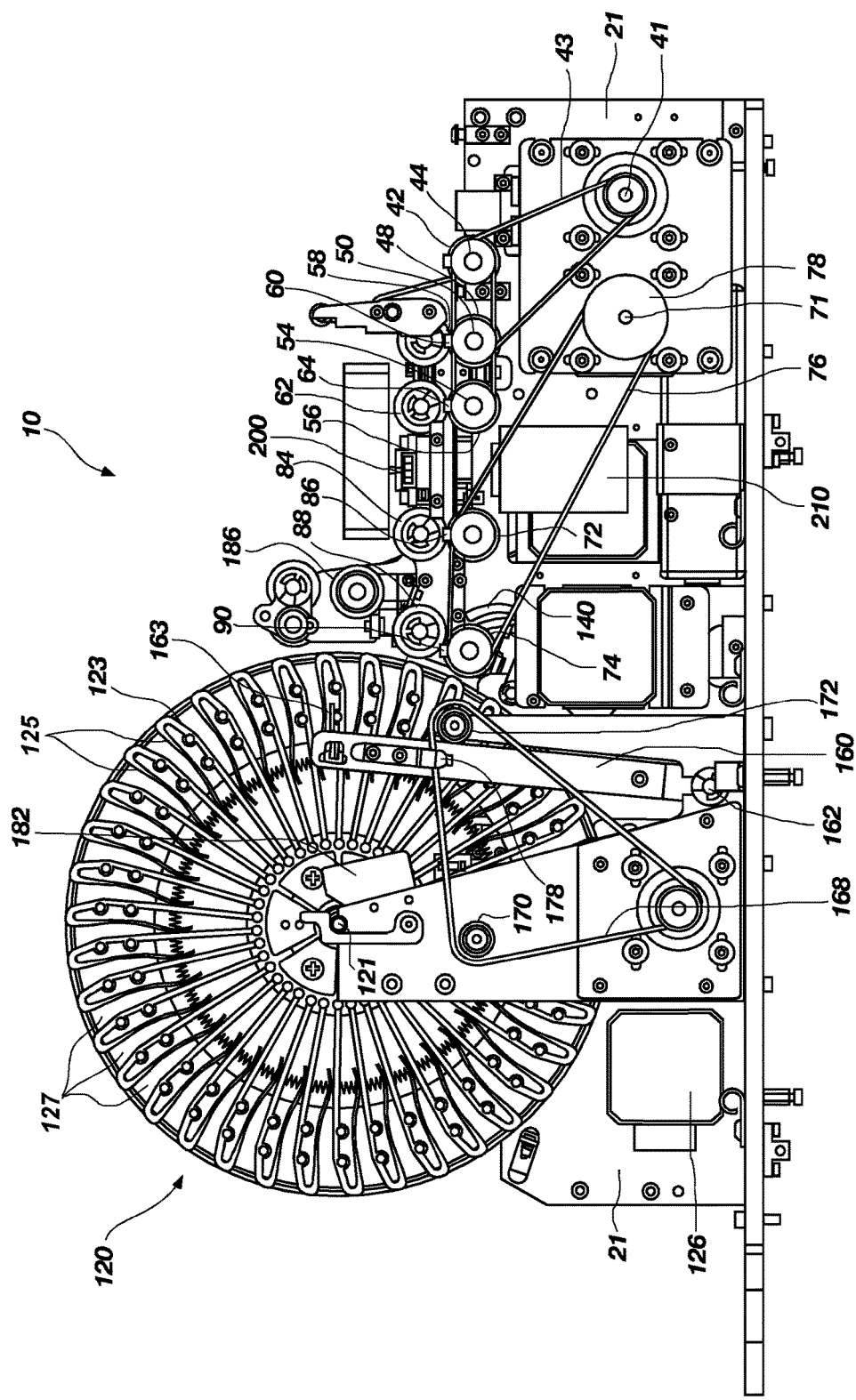
FIG. 4A is a view of a first side elevational view of the card-handling device shown in FIG. 1 with the cover removed to facilitate illustration of active components of the card-handling device.
Figure 4B:
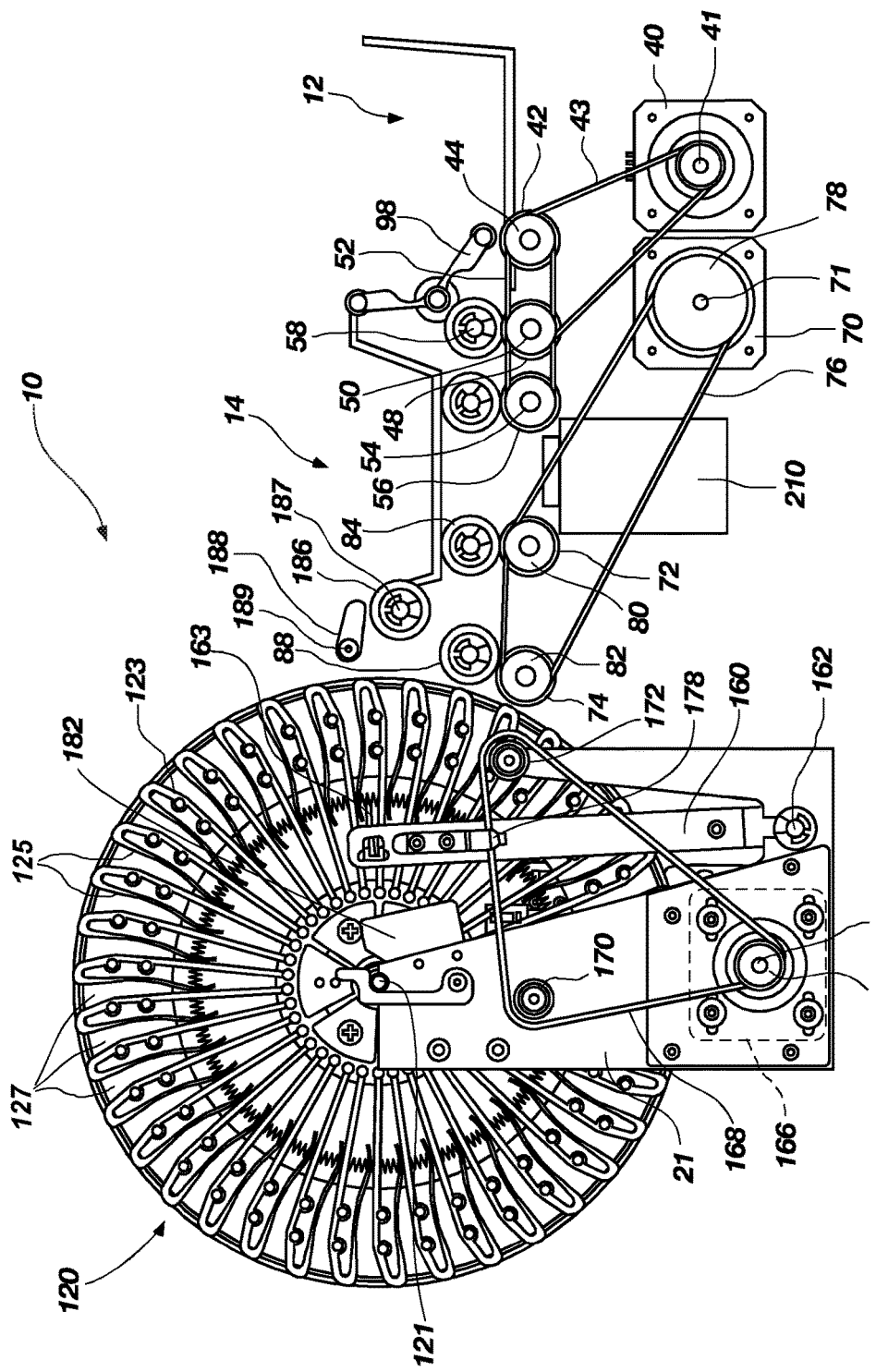
FIG. 4B is a simplified version of FIG. 4A, illustrating only selected elements to facilitate description of those elements.

FIG. 4A is a side view of the card-handling device 10 shown in FIG. 1 with the cover 18 removed. FIG. 4B is a simplified version of FIG. 4A, illustrating only certain elements of the card-handling device 10 to facilitate description thereof. Referring to FIGS. 4A and 4B in combination, the card-handling device 10 may include a card infeed system 240 (FIG. 8) comprising a first drive system and a second drive system.

The first drive system may include a first card infeed motor 40 (FIG. 4B) that is configured to drive rotation of a card feed roller 42 using a first endless toothed belt 43 coupled to both a drive sprocket 44, which is mounted on a drive shaft 41 of the motor 40, and the card feed roller 42. A lowermost card in a stack of spent cards placed in the card infeed tray 12 will come into contact with card feed roller 42. The first card infeed motor 40 is also configured to rotationally drive a first advancing roller 48 using the first endless toothed belt 43. A second endless toothed belt 52 meshes with a sprocket 50 as well as a sprocket 54 on a shaft carrying a second advancing roller 56. In this configuration, as the first card infeed motor 40 drives rotation of the card feed roller 42 and the first advancing roller 48 with the first endless toothed belt 43, the first card infeed motor 40 will also drive rotation of a second advancing roller 56 with a second endless toothed belt 52. First opposing idler roller 58 adjacent the first advancing roller 48 forms a first nip 60 (FIG. 4A), and second opposing idler roller 62 adjacent roller 56 forms a second nip 64 (FIG. 4B). The first opposing idler roller 58 may be adjustable in the vertical direction of FIG. 4A. Cards provided in the card infeed tray 12 (FIG. 4B) may be sequentially moved in the horizontal direction of FIGS. 4A and 4B by the card feed roller 42 into the first nip 60, and subsequently into the second nip 64.

The second drive system may include a second card infeed motor 70 (FIG. 4B) that is configured to drive rotation of a third advancing roller 72 and a fourth advancing roller 74 using a third endless toothed belt 76 that is coupled to a pulley 78 mounted on a drive shaft 71 of the motor 70, a pulley 80 mounted on a shaft carrying the third advancing roller 72, and a pulley 82 mounted on a shaft carrying the fourth advancing roller 74. A third opposing idler roller 84 adjacent the third advancing roller 72 forms a third nip 86 (FIG. 4A), and a fourth opposing idler roller 88 adjacent roller 74 forms a fourth nip 90 (FIG. 4B). The fourth opposing idler roller 88 and the fourth nip 90 may be oriented and configured to deflect a card passing therebetween upwardly and into a compartment 127 or other card storage area of a carousel 120 or other temporary card storage device.

The first card infeed motor 40 and the second card infeed motor 70 each may be operatively controlled by a control system 220 (FIG. 8), which is described in further detail below.

In additional embodiments of the present invention, the card infeed system 240 (FIG. 8) may include only one motor, or more than two motors. Additionally, the card infeed system 240 (FIG. 8) may include any number of advancing rollers and corresponding idler rollers. Furthermore, any means for rotationally driving the card feed roller 42 and the advancing rollers 48, 56, 72, 74 may be used including, for example, gears, sprockets, chains, belts, etc. In yet additional embodiments, the card feed roller 42 and each of the advancing rollers 48, 56, 72, 74 may be directly mounted on a drive shaft of a corresponding motor.

Figure 5:
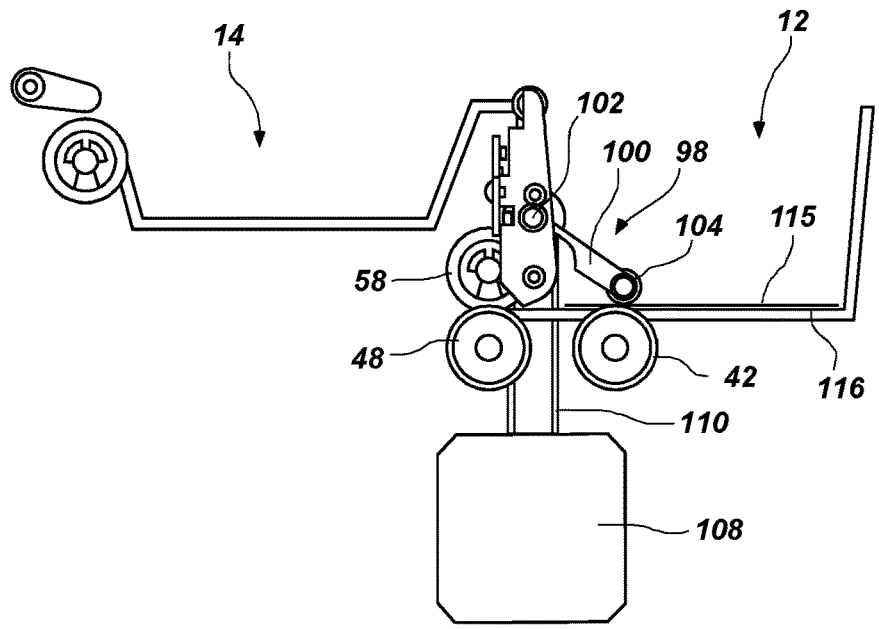
FIG. 5 is an enlarged partial side view of a card infeed tray, card feed roller, and dual function gate of the card-handling device shown in FIG. 1.

Referring to FIG. 5, in some embodiments of the present invention, the card infeed system 240 (FIG. 8) of the card-handling device 10 may further include a gate member 98 operatively associated with the card infeed tray 12. The gate member 98 may comprise an extension arm 100 having a first end that is connected to a shaft 102. The shaft 102 may be rotationally driven by an infeed gate motor 108 and an endless belt 110. A roller 104 may extend substantially transversely from the extension arm 100 (i.e., into the plane of FIG. 5), and may be used to reduce frictional contact with cards 115 in the card infeed tray 12. The roller 104 may be rotationally coupled to the second end of the extension arm 100, and may extend substantially across a width of any cards 115 in the card infeed tray 12 (or a length of any cards 115 in the card infeed tray 12, depending on the orientation of the cards 115 in the card infeed tray 12). In this configuration, the extension arm 100 will pivot about the shaft 102 as the infeed gate motor 108 drives rotation of the shaft 102 using the endless belt 110. The extension arm 100 and roller 104 may be positioned in an upright and retracted pivotal position (not shown) in which the roller 104 does not engage any cards 115 in the card infeed tray 12, to a downwardly angled engaged position in which the roller 104 engages and abuts against the cards 115 in the card infeed tray 12.

Figure 8:
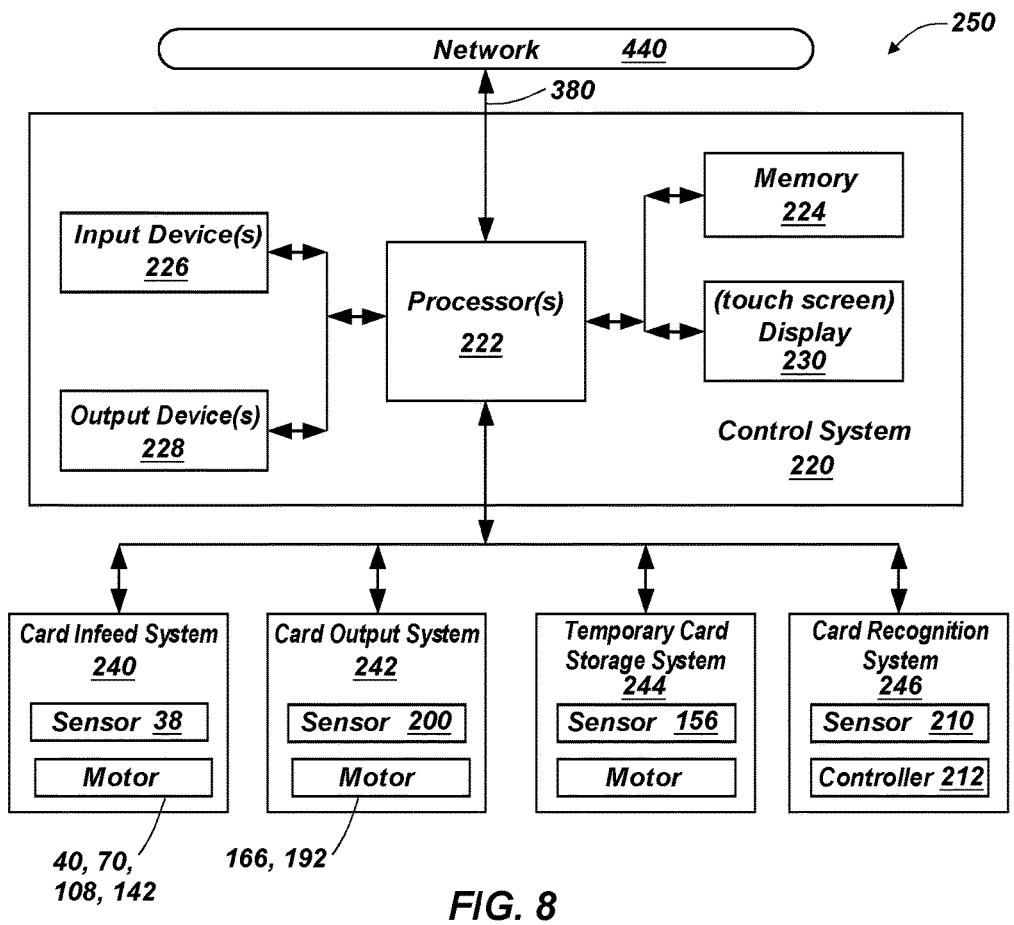
FIG. 8 is a schematic diagram of a control system that may be used in card-handling devices that embody teachings of the present invention, such as that shown in FIG. 1.

The gate member 98 may serve a number of functions. For example, as the number of cards 115 in the card infeed tray 12 is reduced, the weight of the stack of cards 115 in the card infeed tray 12 is reduced, which may reduce the frictional force between the lowermost card 115 in the card infeed tray 12 and the card feed roller 42. The reduced frictional force between the lowermost card 115 in the card infeed tray 12 and the card feed roller 42 may impair the ability of the card feed roller 42 to move the lowermost card 115 to the first advancing roller 48 and to other elements of the card infeed system 240 (FIG. 8). Therefore, the gate member 98 may be used to apply a downward force to the cards 115 in the card infeed tray 12 to maintain the frictional force between the lowermost card 115 in the card infeed tray 12 and the card feed roller 42 above a threshold level. In some embodiments, the gate member 98 may be used to apply a downward force to the cards 115 in the card infeed tray 12 that increases as the number of remaining cards 115 decreases to provide a substantially constant force to the lowest card 115 in the card infeed tray 12. In other words, the gate member 98 provides additional weight against the cards 115 in the card infeed tray 12, which may improve the reliability by which the cards 115 in the card infeed tray 12 are taken into the first nip 60 (FIG. 4A) by the card feed roller 42.

The gate member 98 also may be used to provide a physical separation barrier between cards 115 in the card infeed tray 12 belonging or corresponding to different decks, or between different types of cards (such as regular cards and bonus cards, for example). When the card infeed system 240 (FIG. 8) of the card-handling device 10 is actively moving cards 115 from the card infeed tray 12 to the carousel 120 or other card storage device, the gate member 98 may be in the previously described downwardly engaged position. At the same time, the dealer may be collecting spent cards 115 from the playing table. Because the gate is in the downwardly engaged position, the dealer may put the spent cards (which may correspond to a first deck) in the card infeed tray 12 on top of or over at least a portion of the gate member 98, while the cards previously placed in the card infeed tray 12 (which may correspond to a second, different deck) are being moved from the card infeed tray 12 to the carousel 120 by the card infeed system 240 (FIG. 8). Therefore, in some embodiments of the present invention, a dealer or other user may load cards 115 from a first deck into the card infeed tray 12 while at least some cards 115 from a second deck remain in the card infeed tray 12 without causing or allowing the card-handling device 10 to mix cards from the first deck with cards from the second deck. As a result, the use of the gate member 98 may permit a casino to eliminate use of discard racks (which are typically mounted on gaming table surfaces for holding spent cards until they can be fed into a card-handling device), as spent cards may be placed without delay directly into the card infeed tray 12.

Once the last of the cards 115 below the gate member 98 in the card infeed tray 12 has been removed from the card infeed tray 12 by the card infeed system 240 (FIG. 8), the gate member 98 may be caused to rotate about the shaft 102 to the previously described retracted position to allow any cards 115 previously placed over the gate member 98 in the card infeed tray 12 to fall to the bottom of the card infeed tray 12 adjacent the card feed roller 42. In the retracted position, the gate member 98 may not obstruct the user from inserting additional cards 115 into the card infeed tray 12.

The shaft 102 may be located a selected distance below the upper edge 26 of the card infeed tray 12 (FIG. 1) so that the roller 104 does not extend substantially above the upper edge 26 of the card infeed tray 12 when the gate member 98 is in the previously described retracted position. Furthermore, the shaft 102 may be located a selected distance above the bottom surface 116 of the card infeed tray 12 to enable at least one entire deck of cards 115 to be received in the card infeed tray 12 and allow the roller 104 to abut against the top card 115 in the at least one entire deck of cards 115. Furthermore, the extension arm 100 may have a selected length to provide a distance between the rotational axis of the shaft 102 and the rotational axis of the roller 104 that is short enough that cards 115 provided over the gate member 98 in the card infeed tray 12 will lift and fall to the bottom of the card infeed tray 12 without flipping over as the gate member 98 pivots upwardly in the counterclockwise direction of FIG. 5. A currently preferred gate length is about one-third the length of the cards 115 (or the width of the cards 115, depending on the orientation of the cards 115 in the card infeed tray 12.

The infeed gate motor 108, which is used to selectively rotate the gate member 98, may be operatively controlled by a control system 220, which is described in further detail below.

Referring again to FIG. 4A, the card infeed system 240 (FIG. 8) of the card-handling device 10 may further include a packer arm device 140 for assisting the insertion of a card into a compartment 127 of the carousel 120 or other card storage device. As shown in FIGS. 4A and 4B, each compartment 127 of the carousel 120 may include a leaf spring member 125. As a result, the force of each leaf spring member 125 may need to be overcome as a card is inserted into each compartment 127. The packer arm device 140 may be used to provide additional force to the card as it leaves the fourth advancing roller 74 and corresponding opposing idler roller 88 and enters a compartment 127 of the carousel 120.

Figure 6:
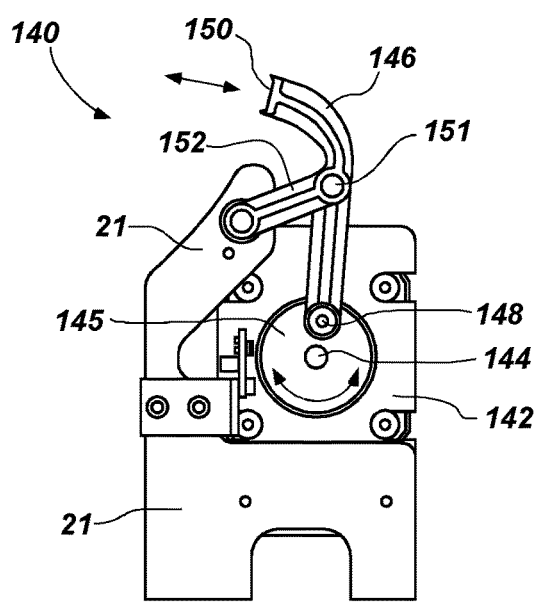
FIG. 6 is an enlarged detailed view of a packer arm assembly of the card-handling device shown in FIG. 1.

FIG. 6 is an enlarged stand-alone view of one embodiment of a packer arm device 140 that may be used in card-handling devices that embody teachings of the present invention, such as the card-handling device 10. As shown in FIG. 6, the packer arm device 140 may include a packer arm motor 142, which may be mounted to the frame 21 of the card-handling device 10. The packer arm motor 142 may be configured to rotate a shaft 144. An eccentric cam member 145 may be mounted to the shaft 144. An elongated packer arm 146 configured as a lever member may be pivotally coupled at a first end 148 thereof to the eccentric cam member 145. The packer arm 146 also may be pivotally attached to a first end of a pivot arm member 152 at an intermediate location 151 along the packer arm 146 between the first end 148 and a second end 150 thereof. A second end of the pivot arm member may be pivotally attached to a frame 21 of the card-handling device 10 or another stationary element of the card-handling device 10.

In this configuration, as the packer arm motor 142 drives rotation of the shaft 144 and eccentric cam member 145 in the direction indicated by the directional arrows shown on the eccentric cam member 145 in FIG. 6, the second end 150 of the elongated packer arm 146 may rock back and forth along an arc-shaped path in the directions indicated by the directional arrows shown proximate the second end 150 of the elongated packer arm 146 in FIG. 6.

The packer arm device 140 may be located in the card-handling device 10 such that the second end 150 of the elongated packer arm will abut against a trailing edge of a card and force the card completely into an aligned compartment 127 of the carousel 120. As the eccentric cam member 145 continues to rotate, the second end 150 of the elongated packer arm 146 may retract to a position that will allow a subsequent card to move past the packer arm device and into position for insertion into a compartment 127 of the carousel 120. In some embodiments of the present invention, the subsequently described control system 220 may cause the packer arm 146 to retract while the carousel 120 is rotating and to extend when the carousel 120 is stationary.

The packer arm motor 142, which is used to selectively move the packer arm 146, also may be operatively controlled by a control system 220, which is described in further detail below.

Referring again to FIG. 4A, as previously discussed, the carousel 120 may include a plurality of compartments 127, each of which may include a leaf spring 125 for holding cards securely within the compartment 127 after insertion. In this configuration, the cards may remain secured within the compartments 127 as the carousel 120 rotates in either the clockwise or counterclockwise direction of FIG. 4A. Each compartment 127 also may have at least one beveled surface 123 for deflecting cards into the aligned compartment 127 during insertion. In some embodiments of the present invention, the compartments 127 of the carousel 120 may be substantially equally sized, and each may be capable of holding up to ten conventional playing cards. By way of example and not limitation, the carousel 120 may include thirty-eight (38) compartments 127. In additional embodiments, the carousel 120 may include fewer than thirty-eight (38) compartments 127 or more than thirty-eight (38) compartments 127.

In some embodiments of the present invention, the previously described card infeed system 240 (FIG. 8) may be capable of selectively inserting a card into a compartment 127 of the carousel 120 either below or above any cards previously inserted and still disposed within that respective compartment. For example, each compartment 127 may have two corresponding card insertion rotational positions of the carousel 120. When the carousel 120 is rotationally positioned in the first of the card insertion rotational positions, any card inserted into the compartment 127 may be inserted below or under any cards previously inserted and still disposed within that respective compartment. When the carousel 120 is rotationally positioned in the second of the card insertion rotational positions, however, any card inserted into the compartment 127 may be inserted above or over any cards previously inserted and still disposed within that respective compartment.

The path that is traveled by a card as it moves from the card infeed tray 12 to a compartment 127 of the carousel 120 is substantially straight and substantially horizontal. In this configuration, the distance traveled by the cards along the path is the shortest distance between the cards in the card infeed tray 12 and the compartment 127 of the carousel 120. The length of this path traveled by the cards may be minimized to minimize the length of the card-handling device 10, and to maximize the speed by which cards may be delivered from the card infeed tray 12 to the carousel 120.

When the card-handling device 10 is mounted on a gaming table such that the flange 30 is substantially flush with the upper gaming surface of the table, approximately the lower half of the carousel 120 may be located beneath the table surface. As a result, the card-handling device 10 may have a relatively low profile on the table.

With continued reference to FIG. 4A, the card-handling device 10 may further include a carousel drive system configured to selectively drive rotation of the carousel member about a shaft 121, by which the carousel 120 is rotatably mounted to the frame 21. The shaft 121 may be mounted to the frame 21 by means of threaded hand screws or a locking releasable mechanism, which may provide for easy removal and replacement of the carousel 120.

Figure 7:
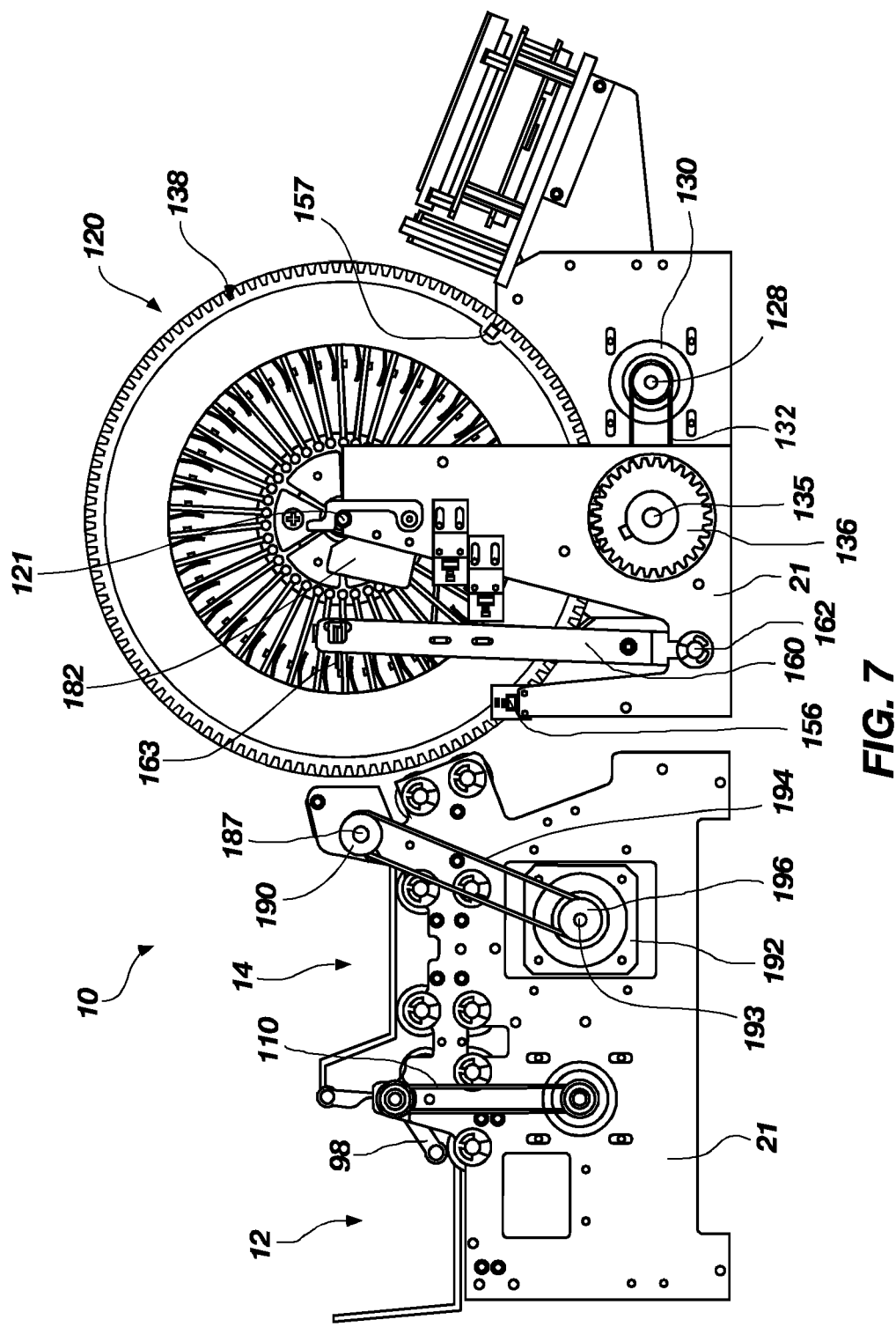
FIG. 7 is a view of a second, opposite side elevational view of the card-handling device shown in FIG. 4A.

The carousel drive system may include, for example, a carousel drive motor 126 that is mounted to the frame 21, as shown in FIG. 4A. FIG. 7 is a view of a second, opposite side of the card-handling device shown in FIG. 4A. By way of example and not limitation, a pulley 130 may be mounted to a drive shaft 128 of the carousel drive motor 126 (FIG. 4A), and another pulley (not shown) may be mounted to a drive shaft 135. An endless belt 132 may be provided around both the pulley 130 and the pulley mounted to the drive shaft 135. In this configuration, as the carousel drive motor 126 drives rotation of the drive shaft 128, the drive shaft 135 will also be rotationally driven by the carousel drive motor 126 and endless belt 132. A pinion gear 136 also may be mounted to the drive shaft 135. The pinion gear 136 may be sized, positioned, and otherwise configured to mesh with a toothed edge or surface 138 provided on the carousel 120. In this configuration, the carousel drive motor 126 may be used to selectively drive rotation of the carousel 120 about the shaft 121 in either the clockwise or counterclockwise direction.

In additional embodiments of the present invention, the carousel drive system may include any means for driving rotation of the carousel 120 including, for example, gears, sprockets, chains, belts, etc.

The carousel drive motor 126, which is used to selectively drive rotation of the carousel 120, also may be operatively controlled by a control system 220, which is described in further detail below.

Referring again to FIG. 4A, the card-handling device 10 may further include a card output system 242 (FIG. 8) for moving cards out from the carousel 120 or other card storage device and into the card output tray 14. The card output system 242 (FIG. 8) may include, for example, an elongated swing arm 160 having a first lower end that is pivotally coupled to the frame 21 using a pin member 162. The swing arm 160 may be configured to pivot about the pin member 162. The second upper end of the elongated swing arm 160 may be equipped or otherwise provide with a retractable inwardly projecting tab 163 (extending into the plane of FIG. 4A) that is configured to extend into a compartment 127 of the carousel 120 while the swing arm 160 is swinging toward the output tray 14, but that retracts before and/or while the swing arm 160 swings back to a resting position in which the swing arm 160 is positioned near an inner circumference 164 of the compartments 127 of the carousel 120. In the extended position, the inwardly projecting tab 163 contacts any cards positioned within the aligned compartment 127 of the carousel 120. The inwardly projecting tab 163 of the swing arm 160 retracts as it comes into contact with a stationary tab 182 mounted to the frame 21.

Referring to FIG. 4B, the card-handling device 10 may include a swing arm drive system, which may include a swing arm drive motor 166, an endless belt 168, a first idler pulley 170, and a second idler pulley 172. The first idler pulley 170 and the second idler pulley 172 may be mounted to the frame 21. The endless belt 168 may extend around a pulley 174 that is mounted to a drive shaft 176 of the swing arm drive motor 166, the first idler pulley 170, and the second idler pulley 172. The endless belt 168 is also securely attached to the swing arm 160 at a location between the first idler pulley 170 and the second idler pulley 172 using, for example, a clamp 178. In this configuration, the swing arm 160 may be selectively swung towards the card output tray 14 by selectively jogging the endless belt 168 around the pulleys 170, 172, 174 in the clockwise direction in FIG. 4B using the swing arm drive motor 166, and the swing arm 160 may be selectively swung away from the card output tray 14 by selectively jogging the endless belt 168 around the pulleys 170, 172, 174 in the counterclockwise direction in FIG. 4B using the swing arm drive motor 166.

The swing arm drive motor 166, which is used to selectively move the swing arm 160, also may be operatively controlled by the control system 220 subsequently described herein.

Referring to FIG. 4B, as the swing arm 160 is caused to swing towards the card output tray 14 and eject a card or cards out from a compartment 127 of the carousel 120, the card may be at least partially forced between a card output roller 186 and an opposing card output idler roller 188. The card output roller 186 may be mounted on a shaft 187. As shown in FIG. 7, a pulley 190 also may be mounted on the shaft 187, and a card output roller drive motor 192 that is attached to the frame 21 may be used to drive rotation of the shaft 187 using an endless belt 194. The endless belt 194 may extend around a pulley 190 mounted on the shaft 187 and another pulley 196 mounted on a drive shaft 193 of the card output roller drive motor 192. In some embodiments of the invention, intermeshing gears may be provided on both the shaft 187 of the card output roller 186 and a shaft 189 of the opposing card output idler roller 188 to ensure that the card output roller 186 and opposing card output idler roller 188 are driven in unison. In this configuration, the card output roller drive motor 192 may be caused to spin the card output roller 186 and opposing card output idler roller 188 as the swing arm 160 is caused to eject a card or cards out from a compartment 127 of the carousel 120 and force the card or cards between the card output roller 186 and the opposing card output idler roller 188. The rotation of the card output roller 186 and an opposing card output idler roller 188 may force and advance the card or cards therebetween into the card output tray 14, where the card or cards may be accessible to a dealer or other user of the card-handling device 10. A sensor 200 (FIG. 4A) may be located and configured to sense or detect when no cards are present in the card output tray 14, and to convey such information to the control system 220 subsequently described herein.

As shown in FIG. 7, one or more sensors 156 may also be provided and configured to detect a relative position of the carousel 120 so as to enable the control system 220 (FIG. 8) subsequently described herein to identify which compartment 127 is aligned to receive a card from the card infeed system 240 and which compartment 127 is aligned for ejection of any cards therein by the card output system 242. By way of example and not limitation, the card-handling device 10 may include one magnetic sensor 156 that is configured to detect a magnet 157 positioned on the carousel 120, as shown in FIG. 7. The position of the carousel 120 when the magnet 157 is positioned adjacent the magnetic sensor 156 may be designated as a "home" position of the carousel 120. The card-handling device 10 may be configured to position the carousel 120 in the home position when the card-handling device 10 is powered on. An encoder that is associated with at least one of the carousel drive motor 126 or the carousel 120 itself then may be used to keep track of the rotational movement of the carousel 120 from the home position, and the information received from the encoder may be used by the control system 220 (FIG. 8) to identify the relative rotational position of the carousel 120 at any given time.

In the embodiment described above, the path each card travels as the card moves from a selected compartment 127 of the carousel 120 into the card output tray 14 (i.e., the card output path) is substantially horizontal and above the path each card travels as the card moves from the card infeed tray 12 to a selected compartment 127 of the carousel 120 (i.e., the card infeed path). In additional embodiments of the present invention, the card infeed path may be positioned vertically above the card output path. This vertical stacking or layering of the card infeed path and the card output path allows both the card infeed tray 12 and the card output tray 12 to be positioned on the same side of the card-handling device 10 (relative to the carousel 120 or other card storage device). In yet additional embodiments, the card infeed path and the card output path may be disposed in substantially the same plane and laterally side by side one another.

Referring to FIGS. 4A and 4B, in embodiments of the present invention, the card-handling device 10 further includes a card sensing system (also referred to as a card recognition system) that is configured to sense at least one identifying characteristic or feature (also referred to as card information) of each card before the card is placed into a compartment 127 of the carousel 120 or other card storage device. By way of example and not limitation, the card recognition system may include a card sensor 210 that is configured to identify at least a rank (e.g., 2, 3, 4 . . . 10, jack, queen, king, ace) and suit (e.g., spade, club, diamond, heart) of a conventional playing card. The sensor 210 may be configured and positioned, for example, to detect the rank and suit of each card as the card passes between the previously described first drive system and second drive system of the card infeed system 240 (FIG. 8) (e.g., as the card passes between the second advancing roller 56 and the third advancing roller 72), as shown in FIGS. 4A and 4B. Of course, those of ordinary skill in the art will recognize that the sensor 210 may be placed at other suitable locations along the path the card travels within the card-handling device 10.

By way of example and not limitation, the card recognition system may include a two-dimensional image sensor comprising, for example, a camera device that includes a complementary metal oxide semiconductor (CMOS) image sensor or a charge-coupled device (CCD) image sensor. For example, the card recognition system may include a video camera imaging system as described (or substantially similar to that described) in U.S. patent application Ser. No. 10/623, 223, filed Jul. 17, 2003 (which was published Apr. 8, 2004 as U.S. Patent Publication No. US2004/0067789A1), the disclosures of each of which are incorporated herein in their entirety by this reference. As described therein, one suitable card recognition system comprises the camera sold under the trademark "DRAGONFLY®" and available from Point Grey Research Inc. of Vancouver, British Columbia, Canada. The DRAGONFLY® camera includes a 6-pin IEEE-1394 interface, and an asynchronous trigger. This camera can be used to acquire images using multiple frame rates, to acquire 640×480 or 1024×724 24-bit true color images, or to acquire 8-bit gray scale images. Furthermore, the DRAGONFLY® camera is typically provided with image acquisition software and exhibits plug-and-play capability. Such a commercially available camera may be combined with commercially available symbol recognition software, which may be executed using an external computer (not shown). Such commercially available image recognition software may be "trained" to identify conventional playing card symbols and to classify and report each acquired image pattern as a specific card suit and rank. The graphics used to identify rank and suit of each card are not identical or standard and may vary between decks of cards. Once an image recognition software program for identifying rank and suit has been developed, the software program may be configured to allow the software program to be trained for each particular deck of cards to be handled by the card-handling device 10 to enable the software program to accurately identify rank and suit of the particular cards used. Such training of the software program may be done at the casino table or by a security team before the card-handling device 10 is placed on a table.

As yet another example, the sensor 210 may include a one-dimensional image sensor such as a line scanning system or device that includes a contact image sensor (CIS), as disclosed in U.S. patent application Ser. No. 11/152,475, filed Jun. 13, 2005, now U.S. Pat. No. 7,769,232, issued Aug. 3, 2010, and U.S. patent application Ser. No. 11/417, 894, filed May 3, 2006, now U.S. Pat. No. 7,593,544, issued Sep. 22, 2009, the disclosures of each of which are incorporated herein in their entirety by this reference. Such line scanning systems may operate in conjunction with additional card position sensors. Sensors that may be used to identify a card position at the time a line scan is performed by the line scanning system are commercially available. Such line scanning systems may be small enough to be entirely incorporated into the card-handling device 10 without requiring used of an external computer for executing an image recognition software program.

Figure 10:
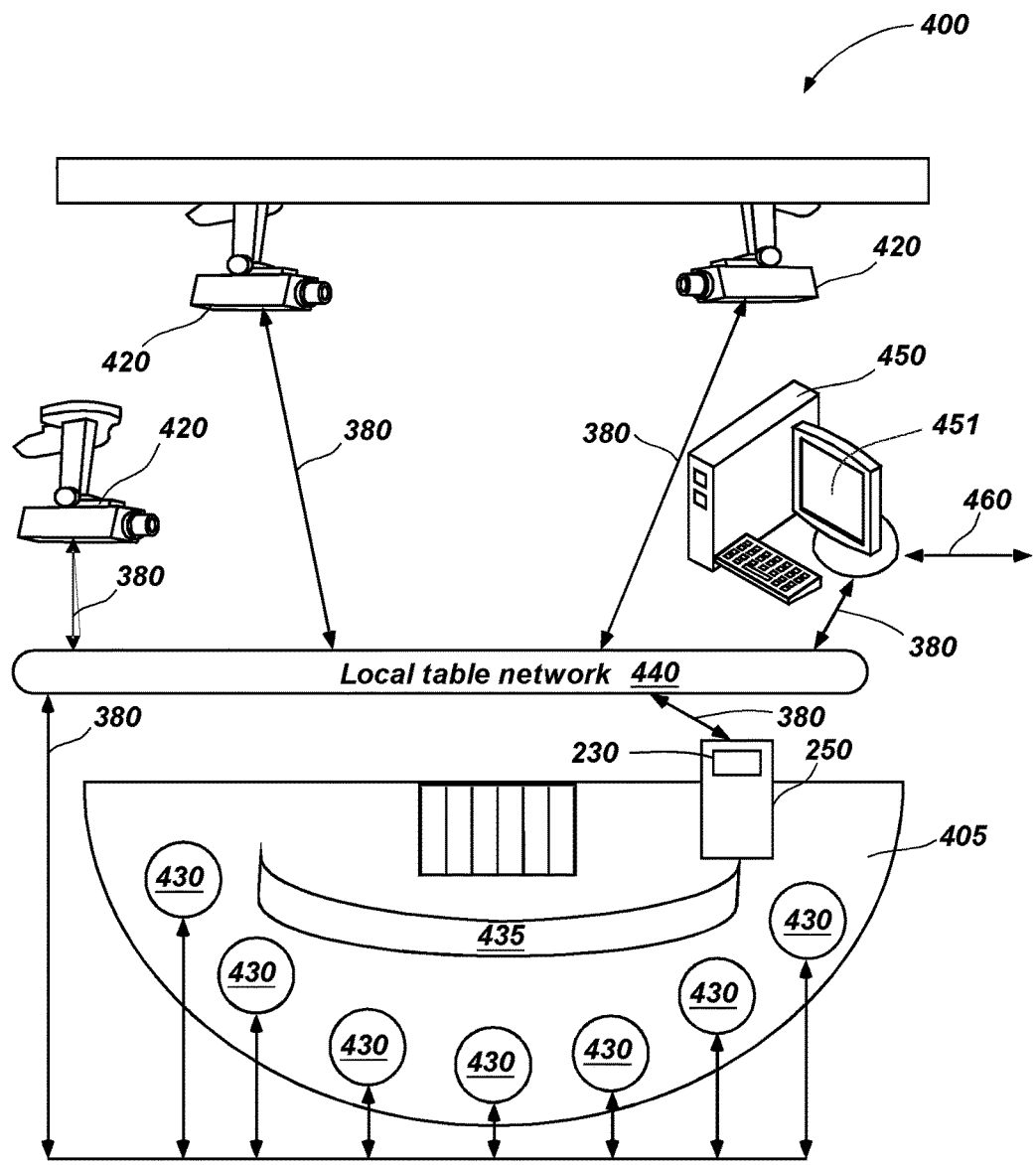
FIG. 10 illustrates a layout of a casino table game and possible placement of elements of an integrated monitoring system used to monitor gaming at a casino table in accordance with embodiments of the present invention.

The sensor signals may be processed by a separate hardware element (not shown) such as a Field Programmable Gate Array (FPGA) or an Application Specific Integrated Circuit (ASIC) using the methodology described in U.S. Patent Publication US 2005/0242500 A1, now U.S. Pat. No. 7,769,232, issued, Aug. 3, 2010, the content of which is incorporated by reference herein. Alternatively, the sensor signals may be processed by a processor 222 (FIG. 8) within the card-handling device 10 or by an external computer system, such as, for example, a table manager 450 (FIG. 10).

In some applications, the cards to be handled by the card-handling device 10 may be standard unmarked conventional cards, and the sensor 210 may be configured to sense and identify only a conventional rank and suit of each card. In additional applications, the cards to be handled by the card-handling device 10 may be marked with ultraviolet (UV), infrared (IR), near infrared (near-IR), or visible wavelength inks or may have embedded radio frequency identification (RFID) tags, magnetic coding, bar codes, embedded electronic devices, or any other marking means, and the sensor 210 may be configured to detect at least one such marking in addition to, or instead of, identifying a rank and suit of each card. The card recognition system also may be configured to sense, detect, and identify cards that have been physically damaged (e.g., due to wear) and/or cards that have been marked in any way that facilitates cheating. The card recognition system may be configured to sense and identify cards that include one or more of cuts, abrasions, bends, dirt, debris, and/or to verify that each card exhibits an expected, predefined color, thickness, reflectivity, mass, or other identifying characteristic or feature.

The card recognition system may be configured to communicate electrically with the subsequently described control system. In addition, multiple sensors 210 may be useful for redundancy, better overall image fidelity, or simply for advantageous placement of the type of sensor. For example, a 2-dimensional sensor may be more practical in a position where it may read the card in a stationary position. On the other hand, the CIS module may be more practical in a position where it reads the card while it is in motion to enable the line scans at various positions along the rank and suit designators on the card.

The card-handling device 10 may further include a control system 220. The control system may configured to receive input signals from a user, to receive input signals from one or more of the various sensors described herein, and/or for selectively controlling one or more of the various previously described active components of the card-handling device 10.

FIG. 8 is a schematic block diagram of one example of a control system 220 that may be used with the card-handling device 10 shown in FIG. 1 to create a card-handling and analysis system 250. In some embodiments, the entire control system 220 may be physically located within the card-handling device 10. In other embodiments, one or more components of the control system 220 may be physically located outside the card-handling device 10. Such components may include, for example, a computer device (e.g., a desktop computer, a laptop computer, a handheld computer (e.g., personal data assistant (PDA), network server, etc.). Such external components may be configured to perform functions such as, for example, image processing, bonus system management, network communication and the like.

As shown in FIG. 8, the control system 220 may include at least one processor 222 (e.g., a microprocessor or microcontroller). The control system 220 also may include memory 224 for storing information such as software and data to be read or written by the processor 222. The control system 220 also may include one or more input devices 226 and one or more output devices 228. By way of example and not limitation, the one or more input devices 226 may include a keypad, a keyboard, a touchpad, a button, a switch, a lever, and the like. An input device 226 may include an authorization element. An authorization element may be used to limit access to some of the functions, such as, for example, recalling the content of current or past hands. As a non-limiting example, authorization element input device 226 may be configured to read the information on a magnetic card strip and send that information to the control system 220. The information on a magnetic card strip may include a user identification. The control system 220 can verify that the card information belongs to a database of authorized users. Other non-limiting examples of authorization elements include a fingerprint scan, a Radio Frequency Identifier (RFID) scan, and a retina scan. A general security element for identifying an authorized user may include one or more authorization elements or it may include one or more authorization elements in combination with the entry of a password by the authorized user.

The authorization element input device 226 may be integrated as a part of the control system 220 or it may be configured as a stand-alone device in communication with the control system 220 across a wired or wireless communication medium.

The one or more output devices 228 may include a graphical display 230 (i.e., a screen or monitor), a printer, one or more light-emitting diodes (LEDs), a device for emitting an audible signal, etc. In some embodiments of the present invention, the input devices 226 and the output devices 228 may be integrated into a single unitary structure, such as, for example, with the display 230 configured as a touch screen display 230.

The touch screen display 230 may be located below the gaming table surface when the card-handling device 10 is mounted to a gaming table in the manner previously described herein. The display 230 may be used to output information to a dealer or other user regarding information such as the identity of the cards that have been dealt into each hand, which may allow the dealer to assess whether the cards shown or played by that player are different (indicating that the cards have been changed or swapped) without alerting the player. For example, if a deviation between a dealt hand and a displayed or played hand were to occur, indicating a confirmed case of card switching, the dealer would be able to notify security without the player's knowledge, which may allow the cheating player to be apprehended. By providing or locating the display 230 below the surface of the table and/or facing away from the players at the table, the display 230 may be concealed to the players, and important information may be conveyed to and from casino personnel without the knowledge of the players. Touch screen controls on the display 230 also may provide a larger number of input options for the user, as compared to more standard push button controls. The display 230 may be capable of displaying alphanumeric information, graphical information, animation, video feed, and the like.

As another input option, the touch screen may be used to present login information for an authorized user. Such information may include a user identification, a password, or a combination thereof. As a non-limiting example, the touch screen may prompt a user to enter a user identification and a password. As another non-limiting example, the presentation and acceptance of login information may be used in combination with the authorization element input device 226 such that the user identification is received from the magnetic card or other authorization element and the password is entered by the authorized user. In this combination, the database of authorized users may be checked to determine that the entered password corresponds with the user identification on the magnetic strip.

As another non-limiting example, the control system 220 may be configured with a factory default password. After entry of the factory default password, custom password information may be entered, such as, for example, to create authorized user passwords. In some embodiments, the default password may only allow access to operations for entering the custom passwords. In these embodiments, entry of a custom password may be required to access hand information.

As shown in FIG. 8, the control system 220 may be configured to communicate with each of the previously described card infeed system 240, card output system 242, temporary card storage system 244 or device, and card recognition system 246. In this configuration, the control system 220 may be configured to receive input signals from a dealer or other user, signals from the various sensors of the card-handling device 10, and to coordinate and control operation of the card infeed system 240, the card output system 242, the temporary card storage system 244, and the card recognition system 246 so as to perform various card-handling operations such as, for example, shuffling of cards placed in the card infeed tray, sorting cards placed in the card infeed tray, and/or forming and sequentially dispensing playing hands from cards placed in the card infeed tray.

The control system 220 may be configured to communicate across any wired or wireless communication medium 380 to a network 440. By way of example, and not limitation, communication media may include serial data links, parallel data links, Ethernet, a Wide Area Network (WAN), a Local Area Network (LAN), BLUETOOTH®, Wi-Fi, WiMax, and other suitable communications links. In some embodiments, communication on the communication medium may be implemented with a substantially stand-alone hardware element (not shown). In other embodiments, the communication may be accomplished with a combination of hardware and firmware/software.

The network 440 also may be used to collect and/or process data from other data collection devices on a gaming table such as, for example, radio frequency identification (RFID) wager amount sensors, object sensors, chip tray inventory sensors, and the like, as is explained more fully below in the description of FIG. 10. Data may be collected by the control system 220 and sent to a remote database for later analysis and processing, or the data may be analyzed in real time.

The processors 222 may be implemented as microcontrollers including memory for storage of data and firmware/software for execution thereon. The processors 222 also may be implemented as microprocessors with separate memory 224 for storage of the data and firmware/software. In addition, the processors 222 may incorporate an ASIC, Field- Programmable Gate Array (FPGA), multiple Programmable Logic Devices (PLD), and combinations thereof.

In some embodiments, the processors 222 may be configured as two separate processors configured to perform different functions. A first processor may be configured for operating and controlling the functions of the shuffler, including operation of electrical devices such as motors, controlling the images displayed on the display 230, processing signals received from all internal sensors such as optical object presence sensors, motion sensors and the like. Thus, during operation, the first processor 222 may determine the random order in which cards are loaded into the compartments of the card-handling device 10.

The first processor may also control the display 230 including touch screen controls and may be configured as a further user interface for programming the processors to display additional game names and to dispense cards according to user inputted data.

A second processor (not shown) may be used to interpret information received from the card recognition system 246 to determine rank, suit, other card information, or combinations thereof. The first processor and the second processor may communicate with each other and collaborate so that the identity of each card and the compartment in which it is placed are associated.

Of course, those of ordinary skill in the art will recognize that with multiple processors 222, the task load may be allocated differently depending on performance characteristics and features of each of the processors 222. For example, a microcontroller may include features well suited for controlling and interfacing with external devices and a microprocessor may be well suited for performing signal processing functions such as image recognition.

In operation of embodiments of the present invention, the dealer will "deal" the hands from the card output tray to each player, such as in a preset order or by player position. Thus, embodiments of the present invention can track the cards from the shuffler to the player to determine the contents of each player's hand. In other words, through data manipulation, information relating to the content of each hand the shuffler dispenses is formed and is retrievable. The information collected from the card-handling device may be time stamped and stored accordingly. Moreover, this information may be stored internally on the card-handling device or on an external computer to provide a recall feature for any hand during a number of completed rounds of play. In some embodiments, a large database outside the shuffler may be maintained so that more history of hands dealt can be stored and later retrieved or analyzed.

As shown in FIG. 8, and as was described earlier, in some embodiments of the present invention, the card recognition system 246 may include a separate controller 212 (e.g., a separate signal processor, such as, for example, an FPGA for receiving signals from the sensor 210 (e.g., camera device or line scanning device)) to determine rank and/or suit of each card being read or sensed by the card recognition system 246. In additional embodiments, such functions may be performed by the processor 222 of the control system 220, or the controller 212 may be a separate controller that is integrated with the control system 220 and located remote from the sensor 210.

The control system 220 of the card-handling device 10 may be configured under control of a computer program to enable a dealer or other user of the card-handling device 10 to perform any one of a number of functions or operations on a deck of cards using the card-handling device 10. The display 230 (or other input device) of the card-handling device 10 may include a menu that allows the dealer or other user to select what functions or operations the card-handling device 10 is to perform on a deck of cards placed in the card infeed tray 12. The functions or operations may include one or more of shuffling operations, sorting operations, and dealing operations, and recall of card information from various hands, rounds, or combinations thereof, as will be explained more fully below.

By way of example and not limitation, one function or operation that may be performed by the card-handling device 10 is a shuffling operation that includes a deck shuffle with the entire shuffled deck output to the card output tray 14. In other words, the control system 220 of the card-handling device 10 may be configured under control of a program to cause the card-handling device 10 to randomly shuffle an entire deck of cards placed in the card infeed tray 12, and to dispense the entire deck of shuffled cards into the card output tray 14.

By way of example and not limitation, the card-handling device 10 may be used to shuffle cards placed in the card infeed tray 12, the control system 220 of the card-handling device 10 may be configured to read or sense one or more identifying characteristics or features of each card as the card is carried past the card recognition system 246, as previously described herein, and to randomly rotate the carousel 120 while inserting the cards to insert cards sequentially into the next compartment 127 of the carousel 120. After all the cards have been randomly placed into compartments 127 of the carousel 120, the control system 220 may cause the carousel 120 to spin or rotate in a step-wise motion as the card output system 242 ejects cards out from the compartments 127 of the carousel 120 either randomly or sequentially. In other words, the cards may be placed in a randomized or shuffled sequence as they are placed into the carousel 120. In this manner, the cards or groups of cards may be provided in the card output tray 14 in a random, shuffled sequence.

Yet another function or operation that may be performed by the card-handling device 10 is a dealing operation that includes a sequential output of randomly generated playing hands (or other subsets of cards) to the card output tray 14, each hand or subset of cards comprising a predetermined number of cards. In other words, the control system 220 of the card-handling device 10 may be configured under control of a program to cause the card-handling device 10 to dispense a first randomly generated playing hand or subset into the card output tray 14. A second randomly generated playing hand may be output to the card output tray 14 after the control system 220 receives a signal from the sensor 200 indicating that the first randomly generated playing hand has been removed from the card output tray 14. This process may continue until a selected number of randomly generated playing hands has been dispensed and removed from the card output tray 14. If the game being played requires other sets of playing cards, such as, for example, a set of flop cards, dealer cards, common cards, extra player cards, etc., such sets of cards also may be generated and dispensed into the card output tray 14 in the sequential manner described above to prevent the sets of cards from being mixed with other playing hands or sets of cards. After the last playing hand or set is delivered, any cards from the deck or decks that remain in compartments 127 of the carousel 120 may be automatically unloaded to the card output tray 14, or the remaining cards may be unloaded to the card output tray 14 upon receiving an input signal from the dealer or other user (for example, an input signal generated by touching a predefined button on the touchpad display 230).

In some embodiments of the present invention, the control system 220 (FIG. 8) of the card-handling device 10 may be programmed to handle a particular deck of cards, such as, for example, a conventional deck of 52 playing cards comprising suits of spades, clubs, diamonds, and hearts, each suit comprising cards ranking 2, 3, 4 . . . 10, jack, queen, king, and ace. By way of example and not limitation, when such a deck of cards is placed into and detected within the card infeed tray 12 of the card-handling device 10, the control system 220 (FIG. 8) may be configured under control of a program to electronically generate a random or shuffled sequence of the deck, and to identify the playing hands (or other subsets of playing cards) that would be generated and dealt if the electronically shuffled deck of cards were actually physically dealt to the players (and the dealer himself) by the dealer. The control system 220 then may assign one compartment 127 of the carousel 120 to each of those hands or subsets of playing cards (which may be referred to as "hand compartments." Then, as the cards are fed into the card-handling device 10 and identified by the card recognition system 246, the control system 220 may cause the carousel 120 to selectively rotate such that any cards corresponding to the hands or subsets are placed within the corresponding hand compartments 127 of the carousel 120. Other cards not corresponding to hands or subsets of cards may be placed in one or more of the other compartments 127 of the carousel 120 not designated as hand compartments. The control system 220 then may cause the card output system to dispense the first hand or subset of cards within the first hand compartment 127 into the card output tray 14. After the dealer has removed the first hand from the card output tray 14 and given that hand to the corresponding first player, the control system 220 then may cause the card output system to dispense the second hand or subset of cards within the second hand compartment 127 into the card output tray 14. This process may continue until a selected number of randomly generated playing hands has been dispensed and removed from the card output tray 14 and dealt to the table.

The display 230 may include a touch screen or other user controls that may be used to program the control system 220 of the card-handling device 10. For example, the card-handling device 10 may be programmed to sequentially deliver a specified number of hands each comprising a specified number of players. Furthermore, the card-handling device 10 may be programmed to deliver a specified number of cards to a dealer, a specified number of flop cards, a bonus hand, common cards, or any other card or cards used in the play of a casino card game. The touch screen or other user controls of the display 230 also may be used to input a name of a game for which the card-handling device has been programmed, so that the name of the programmed game appears on the display 230 in a menu of user selectable games. By employing a control system 220 that is programmable by an end user as described herein, the need for factory programming or re-programming of the card-handling device 10 every time a new casino card game is developed may be eliminated, which may save time, eliminate the need for re-submission of software to various gaming agencies for approval before implementation in a casino, and eliminate the need for upgrading software in the field.

By way of example and not limitation, the card-handling device 10 may be programmed by an end user to deliver cards in a pattern or sequence corresponding to the game of THREE CARD POKER®, which requires that the players and dealer each receive three cards. If a new game that utilizes three player cards (each) and three dealer cards were to be developed in the future, an end user would be able to input information including the new game name into the card-handling device 10 and the card-handling device 10 would be configured for playing such a game without requiring a software change.

Figure 9:
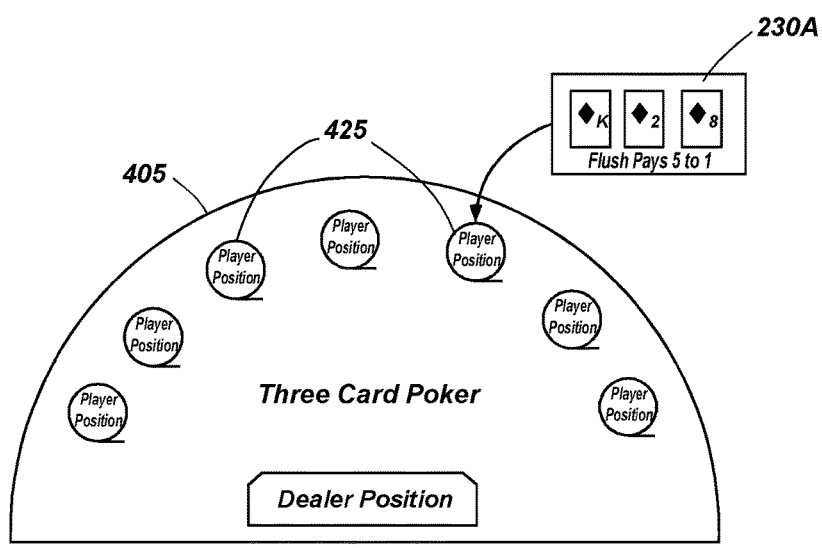
FIG. 9 illustrates a casino table game layout and possible placement of player positions.

As shown in FIG. 9, and also with reference to FIG. 8, the display 230 may be configured to display an image of a game table 405 with various player positions 425, such as the THREE CARD POKER®.

In one embodiment with a touch screen display 230, the card-handling and analysis system 250 may be configured such that the user may touch a region near a specific player position 425 and the display 230 may display card information 230A for the hand at that specific player position 425. Alternatively, each of the player positions 425 may display the card information of the hand at each player position 425.

As a non-limiting example, the content of the graphic may include the name of the game, player positions, dealer position, and even game rules. A user may touch a specific player position that is displayed on the touch screen to reveal the hand to which this position was dealt. The display may also show the result of the game, and the associated payouts, for example, a flush on a "Three Card Poker" table may pay 5 to 1.

As another non-limiting example, the touch screen display content may include navigation buttons such as "past rounds," "current round," "played hands," "unused hands," "back," "forward," and "exit." The Played hands button may be used to display the hands that were actually dealt and bet upon in the current or a previous round. Similarly, the unused hands button may be used to display hands that may have been processed by the shuffler but never used in a round of play.

As non-limiting examples, the back button and forward button may be used to navigate among unused hands or played hands. Similarly, the back button and forward button may be used to navigate among previously played rounds that are stored in a database of rounds.

FIG. 10 is a block diagram of an integrated monitoring system 400 (also referred to as a table management system) used to monitor a gaming table 405 (shown in FIG. 7). The integrated monitoring system 400 includes a card-handling and analysis system 250 coupled to a table manager 450 through a local table network 440. Some embodiments of the integrated monitoring system 400 may also include one or more table image units 420 and object recognition device 430 (e.g., chip readers) coupled to the table manager 450 through the local table network 440. The table manager 450 may be coupled to a server (not shown) through a communication network 460. By way of example, and not limitation, the communication network 460 may be configured to couple multiple table managers 450 to a central database or server by creating a network for a specific pit area, a specific casino floor area, or the entire casino.

The overhead imaging equipment and other hardware and/or software is used to extract game information from a live gaming table. Data from the overhead imaging equipment may be processed to extract game play information. Non-limiting examples of game play information include but are not limited to: player position occupied, wager placed at a given player position, movement of a card or group of cards from a shuffler (or card-reading shoe) to a player position, movement of a card or cards to a common card area, movement of a card or cards to a dealer card area, movement of a card or cards to a bonus card area, placement of a side wager, withdrawal of a wager, rolling of a dice, spinning of a wheel, moving of cards from one area to another area on the table, the collection of cards at the conclusion of a round of play, dealer hand signals, the payment of payouts and the taking of lost wagers, etc.

U.S. patent application Ser. No. 11/558,810, filed Nov. 10, 2006, and titled "Casino Table Game Monitoring System," describes comprehensive card game monitoring systems, including suitable hardware and software for performing the overhead imaging function. Data such as the card composition (for games dealt-face up) and wager information from such a system is collected and used in combination with the hand composition information derived from the card-reading system of shufflers of the present invention to form data records of historical hand composition for a given player position. The content of this application is incorporated by reference in its entirety.

Card composition data from the overhead imaging system may be compared to the card composition information collected in the shuffler to determine if illegal card swapping has occurred. The data from the overhead imaging system can also be used to associate the hand with a particular player position on the table. Additionally, data from the overhead system may be used to verify a hand composition prior to making a large payout.

The combined data may be stored in memory associated with a processor within the card shuffler or transmitted via a hardwire, wireless or network connection to an external database. In one example of the invention, a finite number of hands (i.e., 8-10) per player position is stored in the internal memory of the shuffler and can be displayed on the display associated with the shuffler. Any information that is not stored in the shuffler memory may be instead stored in the external database of an external computer and may be displayed on a display associated with the external computer. In some embodiments, the information stored in the external database may be recalled and displayed using the user inputs of the shuffler, allowing the previously stored information to be displayed on the shuffler display.

A layout of a blackjack table 405 is shown as a non-limiting example of another possible casino table game to which embodiments of the present invention may be applied. The layout illustrates one contemplated, suitable arrangement of elements of the integrated monitoring system 400 in accordance with an embodiment of the invention. The integrated monitoring system 400 may include many components for determining various forms of information about the game being played at the table 405, the players playing the game, wager amounts and payouts, and the dealer responsible for the game. As is described below in more detail, the information may be captured, processed, and acted upon (e.g., generation of alerts) in substantially real time.

In system 400, the table 405 is used for blackjack and is equipped with the card-handling and analysis system 250 (FIG. 8) described earlier. The card-handling and analysis system 250 with display 230 is configured for communications via communication medium 380 and the local table network 440 with the table manager 450. The system 400 may include an object recognition device 430. As one example of an object recognition device 430, FIG. 10 illustrates object recognition devices 430 that may be configured as Radio Frequency Identifier (RFID) antennas/transmitters for each wagering area. In an embodiment with RFID transmitters 430 and RFID tagged chips (not shown), the RFID transmitters 430 are located within or underneath the table 405. The RFID antennas/transmitters respectively read the values of the game chips and then transmit the chip information to the table manager 450 via the communication medium 380 and local table network 440. U.S. Pat. Nos. 5,651,548 and 5,735,742 describe RFID chips and chip reading systems that may be used as the game chips and RFID transmitters 430. Although not shown, the RFID transmitters 430 may be configured to extend into an insurance area 435 of the table 405 to obtain the chip values of insurance wagers. In another embodiment, additional individual RFID transmitters connected to the communication medium 380 may be placed in the insurance area 435, one RFID transmitter associated with each player wagering area.

The system 400 may also include overhead cameras 420 (also referred to as image units) connected to a ceiling of the casino, mounted on a pole to the table, or in the vicinity of the table 405. These cameras 420 process the images received by the cameras 420 respectively and communicate with the table manager 450 over the communication media and the local table network 440.

The table manager 450 processes, and may transmit, images of items viewed by the cameras 420 in substantially near real time. Dealt card values, wagers, and other table activity can be imaged and determined using the cameras 420 in cooperation with the table manager 450. The table manager 450 may be implemented as a general-purpose computer system, a server, or other processor system as is generally known in the art. The table manager 450 will contain computer implemented processing that may be stored on a computer-readable medium of the general-purpose computer system. As such, the processing and functions of the table manager 450 may be stored as a computer program on a computer-readable medium, or downloaded from the server (not shown) over the communication network 460.

As can been seen from FIG. 10, the cameras 420 are positioned to achieve a full view of the gaming table surface, and may be positioned to give the best vantage point for the desired application. An optical or magnetic synchronizing sensor can be used to detect the presence of an object on the gaming surface of the table 405. The sensor, if used, may activate the cameras 420 and trigger image acquisition. The images are processed and transmitted to the table manager 450.

As with the control system 220 (FIG. 8) of the card-handling device 10 (FIG. 1), the integrated monitoring system 400 may be configured with an authorization element input device (not shown). As a non-limiting example, the authorization element may be in communication with the table manager 450. Thus, in the integrated monitoring system 400, the table manager 450 may be configured for handling the authorization process of gathering a user identification, a password, or a combination thereof. The result of the authorization process may then be sent to the card-handling and analysis system 250.

Figure 11:
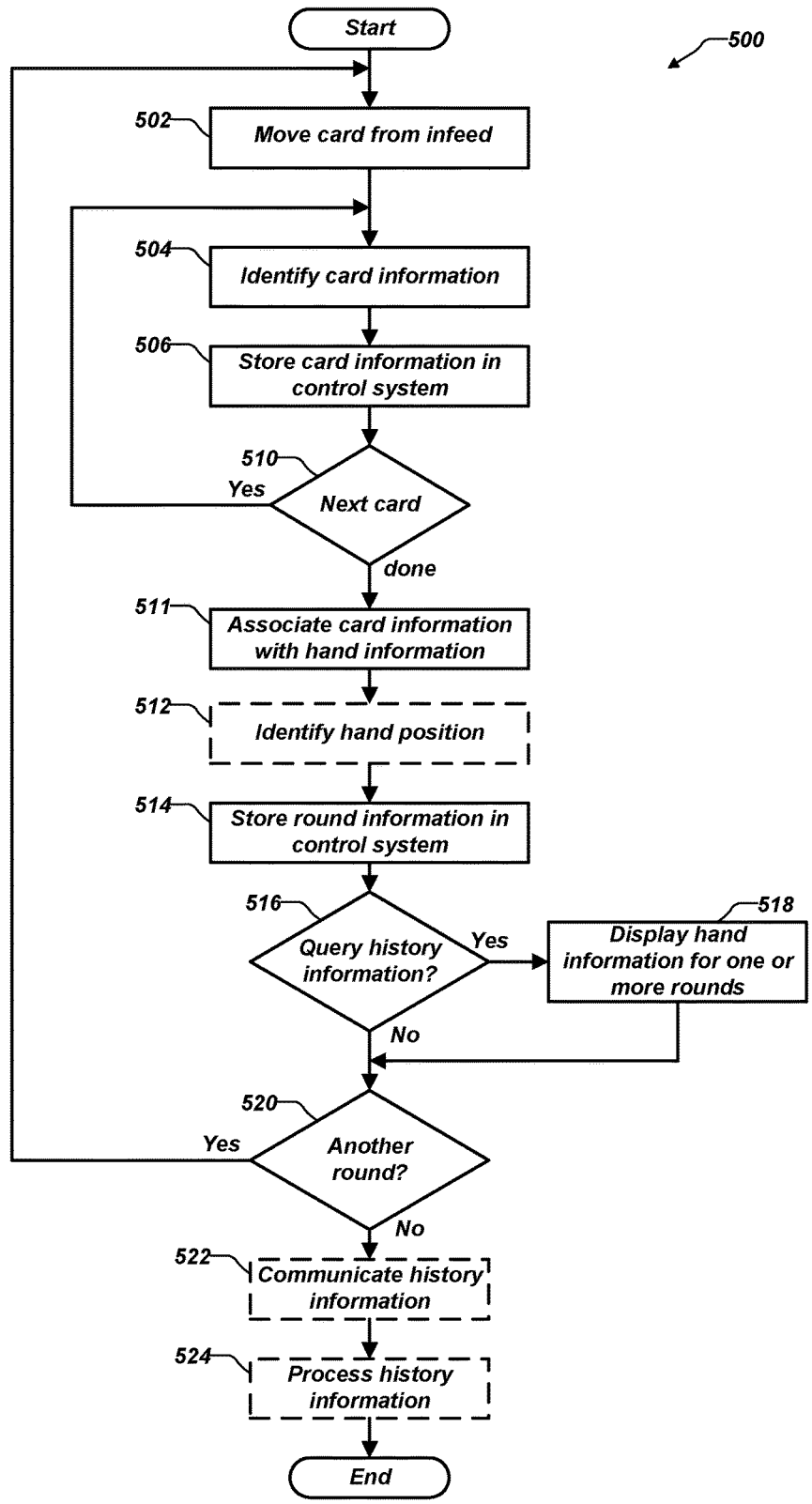
FIG. 11 is a flow diagram of a method of recognizing card information and maintaining a play history in accordance with embodiments of the present invention.

FIG. 11 is a flow diagram of a method of recognizing card information and maintaining a play history in accordance with embodiments of the present invention. Many of the operations illustrated in FIG. 11 may be performed anywhere within the process and are shown in the sequential order of FIG. 11 only for ease of description. At operation 502 the cards are moved from the infeed of the card-handling device and through at least part of the card-handling device. At operation 504, the card recognition system identifies information for each card as it moves through the card-handling device or at some specific location within the card-handling device. Any suitable location within the card-handling device may be used as long as the card information collected may be associated with a specific card and a specific hand or group of cards.

Operation 506 indicates that the card information from the card recognition system may be analyzed to determine card features, such as, for example, rank and suit, and the card information is stored in the control system.

Decision 510 determines whether another card should be processed for the current round. If so, control returns to operation 504 to process the next card. If after loading and the proper number of cards are present for the current round, control continues on to operation 511. The loop controlled by decision 510 may be used, as a non-limiting example, to process each card in a standard 52 card deck to verify that the deck is complete. This may be done by comparing the rank and suit of each card with a library of stored information. If a card is missing from the deck, the rank and suit of that card may be displayed and the shuffle may be aborted.

In other words, as each card is processed by the device, a processor (or process) associated with controlling the card-handling device can track where each card that is handled ends up in the carousel 120 (FIG. 4A). In addition, another processor (or another process) can keep track of the card information for each card. As a result, the loop controlled by decision 510 can verify a full deck is present based on the card information (e.g., rank and suit).

At this point, some embodiments may maintain the process of identifying which card went where in the carousel separate from the process of identifying the card information for each card. As a non-limiting example, suppose the cards are numbered sequentially with a card number as they are delivered to the carousel. The first process may track the random distribution of cards. For example, the first process could track that card 1 is delivered to compartment 8, card 2 is delivered to compartment 3, card 3 is delivered to compartment 1, and so on. The second process may track that card 1 is a two of diamonds, card 2 is a king of clubs, card 3 is a five of hearts and so on. With this tracking, as a security feature, the overall process 500 may not know complete information about what each hand contains. Rather, one process may know that a hand contains cards 3, 8, and 51. The other process may know the specific rank and suit of each card in the sequence of card numbers.

After completion of verification of the deck and recording of card information for each sequential card, control passes to operation 511.

In operation 511 the card information for each sequential card may be associated with the hand information of which card numbers are in which compartments of the carousel. In other words, as a non-limiting example, the information that compartment four contains cards 3, 8 and 51 is combined with the information that card 3 is a queen of hearts, card 8 is a ten of clubs, and card 51 is a nine of spades.

Some embodiments may perform this operation of associating the hand information with the card information as late as possible in the round to prevent cheating where the information may be known before the hands are actually dealt to the players. Thus, the association may be made at different point in execution of playing the round, such as, for example, after the hands are complete in the carousel, as a hand as it is removed from the card-handling device, as a hand is placed in a player position, or after all hands have been dealt.

In other embodiments of the invention, instead of associating the card information of all cards with all the card numbers, the association process may only be performed for the card information associated with cards that are dealt into compartments forming hands. The rank/suit information of the unused cards (i.e., the cards that go into discard compartments) may not be matched up.

In still other embodiments, the card information may be associated directly with the compartment number rather than keeping track of the card information and hand information separate. Either way, after all cards have been distributed, the hand compositions are known by the processor. As a matter of design choice, this information is not viewable to the end user until after the cards have been distributed into the delivery tray.

Optional operation 512 indicates that the hand positions may be identified for the hands before, after, or when they are dealt from the card-handling device. If the embodiment is configured with an object recognition device, the hand position may be determined based on active player positions as is described above with reference to FIG. 10.

Operation 514 indicates that all card information and player position information may be stored for the entire round after the round is complete. As a non-limiting example, such information may include, the type of game, player position, card rank and suit of each card in each player position's hand, size of bet at each player position, and anticipated payout based on the rules.

Decision 516 indicates whether a query is made for history information. This history information may include card information and player position information for the current round or for past, completed rounds. If display of history information is desired, operation 518 displays the desired information. Otherwise, control transfers to decision 520. The display information may include a display of all hands for the current round or only hands at active player positions. Furthermore, the display may be configured to display a single player's current hand or past hands.

In some embodiments, the display may display the card information by presenting some type of graphical representation or symbol for the card information such as rank and suit. In other embodiments, all or part of a stored image of the card may be displayed rather than just the rank and suit symbols. For example, a graphic image of a one-eyed Jack of diamonds can be displayed rather than a "J" and a diamond symbol. In a preferred embodiment, only a portion of the graphic image is displayed (e.g., 25% of the card face).

In addition, the shuffler or an external game controller in communication with the shuffler processor may be programmed with the game rules such that the shuffler can display the game result information or send data to an external display. In a preferred format, the game rules are programmed into the shuffler processor such that the winning hand can be identified on the shuffler display. Even if an external processor determines a game result, the data can be transmitted back to the shuffler so that the game outcome can be displayed on the shuffler display and so that the display can indicate to the dealer who should be paid and the correct payment amount.

Decision 520 indicates whether another round is desired; if so, control transfers back to operation 502, otherwise, control transfers to operation 522. Optional operation 522 indicates that the history information gathered and stored in the control system 220 (FIG. 8) or table manager (FIG. 10) may be transferred to another computer for archiving or additional processing. As a non-limiting example, the control system 220 may include a history of about 10 rounds. If the control system 220 is in communication with an external computer, the control system 220 may send the round information for rounds older than the past 10 rounds to the external computer. Otherwise, the control system 220 may simply drop off the oldest round beyond the 10th round.

Optional operation 524 indicates that additional processing on the history may be performed. Additional processing may include, as non-limiting examples, review of the history in an attempt to find dealer errors, cheating, and statistical review of the history to find betting patterns or to verify randomness of the game. Furthermore, this additional processing may be performed on an external computer, the table manager 450 (FIG. 10) or the control system 220 (FIG. 8). In one embodiment, historical hand composition information is stored within control system 220, and is accessible by the user by inputting a request on user input device 226. A touch screen display 230 displays historical hand information upon request. In one embodiment, multiple historical hand compositions for each player position are viewable.

In another embodiment, historical hand composition information is stored on table manager 450 (e.g., controller) and is displayed on either a separate monitor 451 or on the shuffler display 230.

In some embodiments, a shuffler may be configured to deliver no more hands or other card combinations (such as dealer hands, community cards, bonus hands, bonus cards, etc.) than is necessary to administer the game. For games that do not require the dealer to deal hands to all table positions (regardless of whether there is an active player), the shuffler may receive a signal from the wager sensors (or other sensor denoting an active player position) and limits the hand output to only what is necessary to administer the game. As a non-limiting example, if there are only two players, the shuffler will sense that state and deliver only two hands.

Although the embodiments of the invention may have been described with reference to particular card games, it should be appreciated that they may be applicable to any other casino communal or non-communal card games.

While the embodiments of the invention have been described in detail in connection with preferred embodiments known at the time, the invention is not limited to the disclosed embodiments. Rather, the invention can be modified to incorporate any number of variations, alterations, substitutions, or equivalent arrangements not heretofore described, but which are commensurate with the scope of the invention. Accordingly, the invention is not limited by the foregoing description or drawings, but is only limited by the scope of the appended claims, including equivalents thereof.

What is claimed is:

1. A card apparatus, comprising:
    a card-handling system including internal compartments;
    a card recognition system configured to recognize card information including a rank and a suit of each card passing through the card-handling system; and
    at least one processor operably coupled with the card-handling system and the card recognition system, the at least one processor configured to:
        control the card-handling system to insert cards within the internal compartments prior to being delivered to an output tray;
        maintain a record of the card information separately from a record of position information for each card indicating which internal compartment each card has been inserted; and
        associate the position of each card with its corresponding card information.

2. The card apparatus of claim 1, wherein the at least one processor is configured to control the card-handling system to insert cards within the internal compartments to perform a random shuffle of the cards.

3. The card apparatus of claim 2, wherein the at least one processor is configured to associate the position of each card in an internal compartment with the card information after the random shuffle is completed.

4. The card apparatus of claim 3, wherein the random shuffle is one of a shuffle of an entire deck of cards or a portion of a deck of cards.

5. The card apparatus of claim 1, wherein the at least one processor is configured to control the card-handling system to insert cards within the internal compartments to selectively sort the cards into a predefined order.

6. The card apparatus of claim 1, wherein the at least one processor is configured to control the card-handling system to insert cards within the internal compartments to perform at least one of the following operations: shuffling the cards, arranging the cards into a desired order, verifying completeness of a group of cards, reading special markings on the cards, scanning the cards for unauthorized markings, identifying cards lacking required markings, measuring card wear, decommissioning the cards, applying markings to the cards, scanning the cards for unauthorized electronic devices, delivering special cards, or combinations thereof.

7. The card apparatus of claim 1, further comprising an electronic display operably coupled with the at least one processor, and configured to display historical card information responsive to a query from the at least one processor.

8. The card apparatus of claim 7, wherein the historical card information includes played hands during a past round, or unused hands during a past round.

9. A method for tracking and dealing cards using a card shuffler, the method comprising:
    inserting cards into internal compartments of the card shuffler according to an order determined by a processor of the card shuffler;
    generating a record of card information, using the processor of the card shuffler, indicating a rank and a suit for each card inserted into the internal compartments;
    generating a record of compartment information, using the processor of the card shuffler, indicating a compartment identifier for each card inserted into the internal compartments; and
    associating, using the processor of the card shuffler, the compartment information with the previously uncorrelated card information responsive to an event that occurs after the cards are inserted into the internal compartments of the card shuffler.

10. The method of claim 9, further comprising storing the record of the card information and the record of the compartment information internally within memory of the card shuffler.

11. The method of claim 9, further comprising storing the record of the card information and the record of the compartment information within an external device separate from the card shuffler.

12. The method of claim 9, wherein the event includes at least one of all hands being complete within the internal compartments, a hand being removed from the card shuffler, a hand being placed in a player position, or after all hands being dealt for a round.

13. The method of claim 9, further comprising:
    receiving a request for a history of at least one hand from a prior round, wherein the associating occurs responsive to the request for the history; and displaying the history of the at least one hand including the player position and the card information for the at least one hand on an electronic display of the card shuffler.

14. The method of claim 9, wherein the associating occurs only for the card information associated with cards that are dealt and not for unused cards.

15. The method of claim 9, wherein inserting the cards into internal compartments of the card shuffler is according to a random order generated by the processor of the card shuffler to shuffle the cards.

16. The method of claim 15, wherein inserting the cards into internal compartments of the card shuffler includes forming individual hands of cards within the internal compartments prior to outputting the cards from the card shuffler.

17. The method of claim 9, wherein inserting the cards into internal compartments of the card shuffler is according to a predetermined order generated by the processor of the card shuffler to sort the cards into the predetermined order.

18. A card-handling system, comprising:
a card-handling device including internal compartments;
a card recognition system; and
a processor operably coupled with the card-handling system and the card recognition system, the processor configured to:
assign each internal compartment with a compartment identifier;
cause the card-handling device to insert cards into corresponding internal compartments according to an order determined by the processor;
detect card information for the cards using the card recognition system; and
associate the compartment identifiers and the card information for the cards responsive to an event that occurs after cards are inserted into the internal compartments.

19. The card-handling system of claim 18, wherein the processor is configured to cause the card-handling device to form groups of cards into corresponding internal compartments.

20. The card-handling system of claim 19, wherein:
at least some groups of cards formed within internal compartments are used by the card-handling device during game play;
at least some groups of cards formed within internal compartments are not used by the card-handling device during game play; and
the association of the compartment identifiers and the card information is only performed for cards that are used during game play.

* * * * *

UNITED STATES PATENT AND TRADEMARK OFFICE
CERTIFICATE OF CORRECTION

PATENT NO. : 9,922,502 B2  
APPLICATION NO. : 15/483840  
DATED : March 20, 2018  
INVENTOR(S) : Attila Grauzer et al.

Page 1 of 1

It is certified that error appears in the above-identified patent and that said Letters Patent is hereby corrected as shown below:

On the Title Page

In ITEM (73) Assignee:  change "Balley Gaming, Inc., Las Vegas, NV"
to --Bally Gaming, Inc., Las Vegas, NV--

Signed and Sealed this
Seventeenth Day of April, 2018

Andrei Iancu
*Director of the United States Patent and Trademark Office*